US008821376B2

(12) United States Patent
Tolkowsky

(10) Patent No.: US 8,821,376 B2
(45) Date of Patent: Sep. 2, 2014

(54) DEVICES AND METHODS FOR PERFORMING MEDICAL PROCEDURES IN TREE-LIKE LUMINAL STRUCTURES

(76) Inventor: David Tolkowsky, Tel-Aviv (IL)

( * ) Notice: Subject to any disclaimer, the term of this patent is extended or adjusted under 35 U.S.C. 154(b) by 1211 days.

(21) Appl. No.: 12/527,508

(22) PCT Filed: Mar. 12, 2008

(86) PCT No.: PCT/IL2008/000344
§ 371 (c)(1),
(2), (4) Date: Sep. 18, 2009

(87) PCT Pub. No.: WO2008/111070
PCT Pub. Date: Sep. 18, 2008

(65) Prior Publication Data
US 2010/0041949 A1    Feb. 18, 2010

Related U.S. Application Data

(60) Provisional application No. 60/906,210, filed on Mar. 12, 2007, provisional application No. 60/906,199, filed on Mar. 12, 2007, provisional application No. 60/924,431, filed on May 15, 2007.

(51) Int. Cl.
*A61B 1/00*    (2006.01)
*A61B 1/04*    (2006.01)
(Continued)

(52) U.S. Cl.
CPC .............. *A61B 8/12* (2013.01); *A61B 17/12159* (2013.01); *A61B 6/466* (2013.01); *A61B 5/7285* (2013.01); *A61B 2019/5276* (2013.01); *A61B 19/52* (2013.01); *A61B 6/5247* (2013.01); *A61B 19/5212* (2013.01); *A61B 6/541* (2013.01); *A61B 8/5238* (2013.01); *A61B 5/064* (2013.01); *A61B 2019/505* (2013.01); *A61B 2019/5234* (2013.01); *A61B 8/543* (2013.01); *A61B 1/018* (2013.01); *A61B 1/2676* (2013.01); *A61B 1/0052* (2013.01); *A61B 2019/5251* (2013.01); *A61B 17/00491* (2013.01); *A61B 17/12104* (2013.01); *A61B 6/03* (2013.01); *A61B 19/5244* (2013.01); *A61B 2019/5289* (2013.01); *A61B 2019/5291* (2013.01); *A61B 2017/1205* (2013.01)
USPC ........... 600/104; 600/101; 600/106; 600/114; 600/117; 600/156

(58) Field of Classification Search
CPC ............. A61B 1/0008; A61B 1/00082; A61B 1/00087; A61B 1/012; A61B 1/0125; A61B 1/015; A61B 1/018; A61B 1/00137; A61B 1/2676; A61B 17/12022; A61B 17/12104; A61B 17/12131; A61B 19/56; A61B 19/5244; A61B 2017/0034; A61B 2017/5251; A61M 25/00
USPC ......... 600/104, 116–117, 127, 156, 414, 415, 600/424–427, 435, 106, 109; 606/108; 128/207.16
See application file for complete search history.

(56) References Cited

U.S. PATENT DOCUMENTS 3,470,876 A    10/1969    Barchilon
4,017,858 A    4/1977    Kuypers
(Continued)

FOREIGN PATENT DOCUMENTS

WO    WO 2008/111070    9/2008

OTHER PUBLICATIONS

A Supplementary European Search Report dated Feb. 1, 2011, which issued during the prosecution of Applicant's European Patent Application No. 08719969.

(Continued)

*Primary Examiner* — John P Leubecker
*Assistant Examiner* — Arnaldo Torres Diaz
(74) *Attorney, Agent, or Firm* — Sughrue Mion, PLLC

(57) ABSTRACT

Apparatus is described for use with an imaging device (31) that acquires a pre-procedure image of a portion of a subject's body disposed at a pre-procedure position. An input unit receives from a user an indication of two or more lines within the image that correspond to respective branches of a multi-branch luminal structure. A probe (1) moves within the portion along two or more lines in the structure that respectively correspond to the two or more lines within the image. A location sensor (18) coupled to the probe senses location coordinates along the two or more lines, while the portion is at a current position. A control unit (34) registers the image of the portion with the portion's current position by registering (a) the two or more lines within the image, with (b) the location coordinates along the two or more lines. Other embodiments are also described.

29 Claims, 8 Drawing Sheets

Figure 1A:
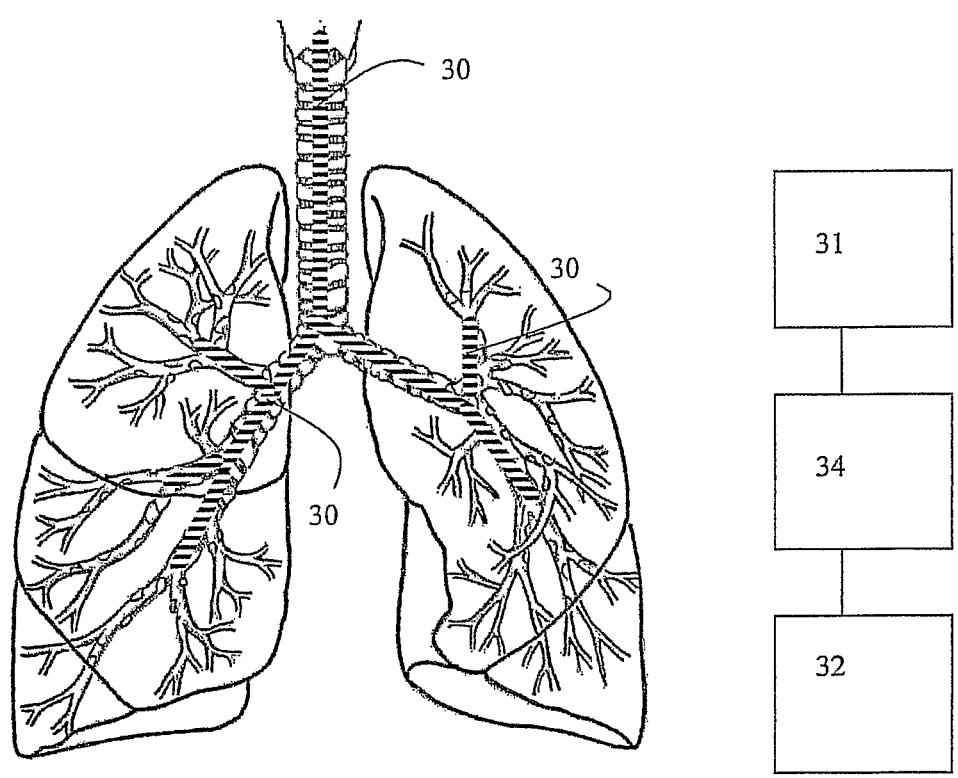

(51) Int. Cl.

| | | |
|---|---|---|
| *A61B 17/12* | (2006.01) | |
| *A61B 6/00* | (2006.01) | |
| *A61B 8/08* | (2006.01) | |
| *A61B 5/06* | (2006.01) | |
| *A61B 1/267* | (2006.01) | |
| *A61B 1/005* | (2006.01) | |
| *A61B 8/12* | (2006.01) | |
| *A61B 5/00* | (2006.01) | |
| *A61B 19/00* | (2006.01) | |
| *A61B 8/00* | (2006.01) | |
| *A61B 1/018* | (2006.01) | |
| *A61B 17/00* | (2006.01) | |
| *A61B 6/03* | (2006.01) | |

(56) References Cited

U.S. PATENT DOCUMENTS

| | | | |
|---|---|---|---|
| 4,849,692 A | 7/1989 | Blood | |
| 4,976,710 A * | 12/1990 | Mackin | 606/15 |
| 5,553,611 A | 9/1996 | Budd et al. | |
| 5,558,091 A | 9/1996 | Acker et al. | |
| 5,636,255 A | 6/1997 | Ellis | |
| 5,697,377 A | 12/1997 | Wittkampf | |
| 5,729,129 A | 3/1998 | Acker | |
| 5,744,953 A | 4/1998 | Hansen | |
| 5,873,822 A | 2/1999 | Ferre et al. | |
| 5,902,239 A | 5/1999 | Buurman | |
| 5,920,319 A | 7/1999 | Vining et al. | |
| 6,016,439 A | 1/2000 | Acker | |
| 6,019,724 A | 2/2000 | Gronninsaeter et al. | |
| 6,226,543 B1 | 5/2001 | Gilboa et al. | |
| 6,233,476 B1 | 5/2001 | Strommer et al. | |
| 6,253,770 B1 | 7/2001 | Acker et al. | |
| 6,445,943 B1 | 9/2002 | Ferre et al. | |
| 6,490,474 B1 | 12/2002 | Willis et al. | |
| 6,592,520 B1 | 7/2003 | Peszynski et al. | |
| 6,593,884 B1 | 7/2003 | Gilboa et al. | |
| 6,610,007 B2 * | 8/2003 | Belson et al. | 600/146 |
| 6,636,757 B1 | 10/2003 | Jascob et al. | |
| 6,711,429 B1 | 3/2004 | Gilboa et al. | |
| 6,782,287 B2 | 8/2004 | Grzeszczuk et al. | |
| 6,783,536 B2 | 8/2004 | Vilsmeier et al. | |
| 6,784,660 B2 | 8/2004 | Ashe | |
| 6,836,745 B2 | 12/2004 | Seiler et al. | |
| 6,892,090 B2 | 5/2005 | Verard et al. | |
| 6,901,927 B2 | 6/2005 | Deem | |
| 6,947,788 B2 | 9/2005 | Gilboa et al. | |
| 6,990,427 B2 | 1/2006 | Kirsch et al. | |
| 6,994,094 B2 | 2/2006 | Schwartz | |
| 6,996,430 B1 | 2/2006 | Gilboa et al. | |
| 7,165,548 B2 | 1/2007 | Deem | |
| 8,106,905 B2 * | 1/2012 | Markowitz et al. | 345/419 |
| 8,239,001 B2 * | 8/2012 | Verard et al. | 600/424 |
| 8,273,013 B2 * | 9/2012 | Niwa et al. | 600/115 |
| 2002/0062120 A1 | 5/2002 | Perkins et al. | |
| 2002/0065512 A1 * | 5/2002 | Fjield et al. | 606/27 |
| 2003/0070682 A1 | 4/2003 | Wilson et al. | |
| 2004/0000314 A1 * | 1/2004 | Angel | 128/207.14 |
| 2004/0097805 A1 * | 5/2004 | Verard et al. | 600/428 |
| 2004/0123868 A1 * | 7/2004 | Rutter | 128/207.14 |
| 2004/0249267 A1 * | 12/2004 | Gilboa | 600/424 |
| 2005/0033149 A1 * | 2/2005 | Strommer et al. | 600/407 |
| 2005/0085715 A1 | 4/2005 | Dukesherer et al. | |
| 2005/0171508 A1 * | 8/2005 | Gilboa | 604/528 |
| 2005/0182319 A1 * | 8/2005 | Glossop | 600/424 |
| 2005/0288684 A1 | 12/2005 | Aronson et al. | |
| 2006/0076023 A1 * | 4/2006 | Rapacki et al. | 128/207.15 |
| 2006/0081255 A1 * | 4/2006 | Miller et al. | 128/207.14 |
| 2006/0084839 A1 * | 4/2006 | Mourlas et al. | 600/116 |
| 2006/0173291 A1 | 8/2006 | Glossop | |
| 2006/0174870 A1 * | 8/2006 | Deem et al. | 128/200.26 |
| 2006/0174893 A1 * | 8/2006 | Kanowitz | 128/207.14 |
| 2006/0184016 A1 * | 8/2006 | Glossop | 600/434 |
| 2006/0207604 A1 * | 9/2006 | Nelson et al. | 128/207.14 |
| 2006/0283462 A1 * | 12/2006 | Fields et al. | 128/207.14 |
| 2007/0015997 A1 * | 1/2007 | Higgins et al. | 600/407 |
| 2007/0055090 A1 | 3/2007 | Neustadter et al. | |
| 2007/0055128 A1 * | 3/2007 | Glossop | 600/407 |
| 2007/0205373 A1 | 9/2007 | Kornblau et al. | |
| 2007/0225559 A1 * | 9/2007 | Clerc et al. | 600/117 |
| 2007/0276180 A1 | 11/2007 | Greenburg et al. | |
| 2007/0293721 A1 * | 12/2007 | Gilboa | 600/117 |
| 2008/0015569 A1 * | 1/2008 | Saadat et al. | 606/41 |
| 2008/0119727 A1 * | 5/2008 | Barbagli et al. | 600/424 |
| 2008/0167614 A1 | 7/2008 | Tolkowsky et al. | |
| 2010/0172556 A1 * | 7/2010 | Cohen et al. | 382/128 |
| 2012/0065481 A1 * | 3/2012 | Hunter et al. | 600/301 |

OTHER PUBLICATIONS

An Examination Report dated Jan. 24, 2012, which issued during the prosecution of Applicant's European App No. 08719969.

"Real-time Bronchoscope Tip Localization Enables Three-dimensional CT Image Guidance for Transbronchial Needle Aspiration in Swine" by Solomon et al. (CHEST, Nov. 1998).

"3D CT-Guided Bronchoscopy with Real-Time Electromagnetic Position Sensor" by Solomon et al. (CHEST, Dec. 2000).

"Computed Tomographic (Holography and Virtual Colonoscopy)" by Ahlquist et al., (Gastrointestinal Endoscopy Clinics of North America, Jul. 1997, pp. 439-452)—an abstract.

A Virtual Bronchoscopic Navigation-System for Pulmonary Peripheral Lesions by Asano et al. (CHEST, 2006, 130:559-556).

"Multimodality Bronchoscopic Diagnosis of Peripheral Lung Lesions: A Randomized Controlled Trial," by Eberhardt et al. (American Journal of Respiratory and Critical Care Medicine Vol 176. pp. 36-41, 2007)—an abstract.

"Electromagnetic Navigation during Flexible Bronchoscopy," by Schwartz et al. (Respiration 2003;70:516-522).

"Electromagnetic Catheter Navigation During Bronchoscopy," by Hautmann et al. (Chest. 2005; 128:382-387).

An Examination Report dated Oct. 22, 2012, which issued during the prosecution of Applicant's European App No. 08719969.

An Examination Report dated Aug. 8, 2013, which issued during the prosecution of Applicant's European App No. 08719969.1.

* cited by examiner

DEVICES AND METHODS FOR PERFORMING MEDICAL PROCEDURES IN TREE-LIKE LUMINAL STRUCTURES

CROSS-REFERENCES TO RELATED APPLICATIONS

The present patent application is a U.S. national phase of PCT Application No. PCT/IL2008/000344 to Tolkowsky, filed Mar. 12, 2008, which is incorporated herein by reference, and which claims the benefit of (a) U.S. Provisional Patent Application No. 60/906,210, filed Mar. 12, 2007, named "Apparatuses And Methods For Registering An Image To A Body Lumen, Tract Or Cavity," (b) U.S. Provisional Patent Application No. 60/906,199, filed Mar. 12, 2007, named "Maneuverable And Localizable Sheath Devices And Methods For Use Thereof," and (c) U.S. Provisional Patent Application No. 60/924,431, filed May 15, 2007, named "Devices and Methods for Performing Medical Procedures in Tree-like Luminal Structures," all to Tolkowsky, and all of which applications are incorporated herein by reference.

FIELD OF THIS INVENTION

The present invention generally relates to medical apparatus. Specifically, the present invention relates to performing medical procedures in tree-like luminal structures.

BACKGROUND TO THE INVENTION

In the course of image-guided navigation, a probe typically comprising one or more location sensors can be navigated along desired paths and/or to desired destinations within a body organ while its updated location is being superimposed on an image of that organ.

Image-guided navigation systems utilizing a probe comprising one or more location sensors are generally known in prior art.

U.S. Pat. No. 6,711,429 to Gilboa et al., which is incorporated herein by reference, describes a system and method for displaying at least one point-of-interest of a body during an intra-body medical procedure. The method is effected by (a) establishing a location of the body; (b) establishing a location of an imaging instrument being for imaging at least a portion of the body; (c) defining at least one projection plane being in relation to a projection plane of the imaging instrument; (d) acquiring at least one point-of-interest of the body; and (e) projecting said at least one point-of-interest on said at least one projection plane; such that, in the course of the procedure, the locations of the body and the imaging instrument are known, thereby the at least one point-of-interest is projectable on the at least one projection plane even in cases whereby a relative location of the body and the imaging instrument are changed.

U.S. Pat. No. 6,226,543 to Gilboa et al., which is incorporated herein by reference, describes a method of recording and displaying in the context of an image a location of at least one point-of-interest in a body during an intra-body medical procedure. The method is effected by (a) establishing a location of the body; (b) inserting at least one catheter into a portion of the body, the at least one catheter including a first location implement; (c) using an imaging instrument for imaging the portion of the body; (d) establishing a location of the imaging instrument; (e) advancing the at least one catheter to at least one point-of-interest in the portion of the body and via a locating implement recording a location of the at least one point-of-interest; and (f) displaying and highlighting the at least one point-of-interest in the context of an image of the portion of the body, the image being generated by the imaging instrument; such that, in the course of the procedure, the locations of the body, the at least one catheter and the imaging instrument are known, thereby the at least one point-of-interest is projectable and displayable in the context of the image, even in cases where a relative location of the body and the imaging instrument are changed.

U.S. Pat. No. 5,558,091 to Acker et al. which is incorporated herein by reference, describes a magnetic position and orientation determining system, with which a representation of a probe can be superposed on a separately acquired image of a subject to show the position and orientation of the probe with respect to the subject.

U.S. Pat. No. 6,233,476 to Strommer et al., which is incorporated herein by reference, describes a medical device comprising a housing, a magnetic detection probe for detecting a plurality of magnetic fields, a biometric unit and a controller, connected to the magnetic detection probe, the biometric unit and the storage unit, wherein the controller receives magnetic field detection information from the magnetic detection probe, and wherein the controller operates the biometric unit in association with the magnetic field detection information.

U.S. Pat. No. 6,593,884 to Gilboa et al., which is incorporated herein by reference, describes a system and method for tracking the position and orientation of a probe, such as a catheter. Three at least partly overlapping planar antennas are used to transmit electromagnetic radiation simultaneously, with the radiation transmitted by each antenna having its own spectrum. A receiver inside the probe includes sensors of the three components of the transmitted field, with sensors for at least two of the three components being pairs of sensors, such as coils, on opposite sides of a common reference point. In one variant of the receiver, the coils are collinear and are wound about cores that are mounted in pairs of diametrically opposed apertures in the housing of the probe. Each member of a pair of coils that sense the same component of the transmitted field is connected to a different input of a differential amplifier. The position and orientation of the receiver relative to the antennas are determined noniteratively.

US Patent Application 2007/0055128 A1 to Glossop, which is incorporated herein by reference, describes a method and system for performing an image-guided endoscopic medical procedure. The method is described as including registering image-space coordinates of a path of a medical instrument within the anatomy of a patient to patient-space coordinates of the path of the medical instrument within the anatomy of the patient. In some embodiments, the image space coordinates of the path of the medical instrument are described as predicted coordinates such as, for example, a calculated centerline through a conduit-like organ, or a calculated "most likely path" of the medical instrument within the anatomy of the patient. In other embodiments, the path of the medical instrument is described as being an actual path determined using intra-operative images of the patient's anatomy with the medical instrument inserted therein. The registered instrument is described as then being navigated to one or more items of interest for performance of the endoscopic medical procedure.

U.S. Pat. No. 5,553,611 to Budd et al., which is incorporated herein by reference, describes a method including the collection of measurements that are taken from a set of measurement electrodes to determine the position of a catheter in a heart chamber.

U.S. Pat. No. 6,994,094 to Schwartz, which is incorporated herein by reference, describes a method for performing a procedure at the fossa ovalis in the septal wall of the heart, which includes the steps of providing a sheath having a body wherein the body has a lumen extending therethrough and an open end at the distal end of the body. The body also has at least one electrode and a position sensor at the distal end of the body. The position sensor generates signals indicative of the location of the distal end of the body. The sheath is navigated to the septal wall using the position sensor, and the fossa ovalis in the septal wall is identified using the at least one electrode of the sheath.

U.S. Pat. No. 6,253,770 to Acker et al., which is incorporated herein by reference, describes a catheter with a lumen wherein the lumen is obstructed by a portion of the catheter. The catheter includes a position detector at the tip of the catheter.

US Patent Application 2005/0171508 to Gilboa, which is incorporated herein by reference, describes a method for guiding an apparatus to a location within the body. The method includes providing a sheath having a lumen and inserting along the lumen a position sensor such that said position sensor is located within, or adjacent to, a distal portion of the sheath. Position information generated using the position sensor is then employed during guiding of the distal portion of the sheath to the location within the body. Once the sheath is in place, the position sensor is withdrawn along the lumen to free the lumen for guiding an apparatus to the location within the body. The position sensor is described as preferably being part of a six-degrees-of-freedom position sensing system. A corresponding catheter system is described as typically including at least one, and preferably two, steering mechanisms. At least one of the steering mechanisms is described as being deployed in a separate center-support distally with respect to the position sensor.

US Patent Application 2006/0184016 to Glossop, which is incorporated herein by reference, describes methods and apparatus for navigating a medical instrument to a target in the lung. In one embodiment, the method includes inserting a bronchoscope into the lung, inserting a catheter into the lung through the working channel of the bronchoscope, inserting a tracked navigation instrument wire into the lung through the catheter, navigating the tracked navigation instrument through the lung to the target, advancing the catheter over the tracked navigation instrument to the target, removing the tracked navigation instrument from the catheter, and inserting a medical instrument into the catheter, thus bringing the medical instrument in proximity to the target.

The use of images generated by multiple sources may in many cases provide clinical value that is greater than the one provided by any of these images alone. While some image-guided medical procedures make use of a single source of imaging, others combine imaging generated by multiple sources of imaging.

U.S. Pat. No. 6,019,724 to Gronningsaeter et al., which is incorporated herein by reference, describes a method for ultrasound guidance during medical procedures, wherein the location of a surgical tool, therapeutic radiation field or a diagnostic energy field is related to the coordinate system of an intra-operative 2D and/or 3D ultrasound imaging system and, optionally, to pre-operative MR/CT/X-ray data.

U.S. Pat. No. 6,996,430 to Gilboa et al., which is incorporated herein by reference, describes a method of displaying cross-sectional images of a body so as to render the cross-sectional images more interpretable.

US Patent Application 2005/0033149 to Strommer et al., which is incorporated herein by reference, describes a method and system for registering a first image with a second image, the system including a first medical positioning system for detecting a first position and orientation of the body of a patient, a second medical positioning system for detecting a second position and orientation of the body, and a registering module coupled with a second imager and with the second medical positioning system, the first medical positioning system being associated with and coupled with a first imager, the first imager acquiring the first image from the body, the first imager producing the first image by associating the first image with the first position and orientation, the second medical positioning system being associated with and coupled with the second imager, the second imager acquiring the second image and associating the second image with the second position and orientation, the registering module registering the first image with the second image, according to the first position and orientation and the second position and orientation.

Typically, an early step in an image-guided procedure is the registration of images to the patient's body. After registration a probe comprising one or more location sensors can be navigated along desired paths and/or to desired destinations in the body organ while its updated location is being superimposed on the image.

The process of registration is aimed at bringing the image and the body organ into the same reference frame of coordinates. It is typically performed by correlating known marked points (also known as markers, or fiducials) in the image with the corresponding observable points in the actual body organ. The locations of the fiducials in the actual organ are typically recorded by physically arriving at them with a probe equipped with one or more location sensors.

Fiducials or markers that are generally known in prior art in the context of image-to-body registration are typically categorized as either 'artificial' or 'natural.' The latter are also known as 'anatomical.'

An article entitled "Real-time Bronchoscope Tip Localization Enables Three-dimensional CT Image Guidance for Transbronchial Needle Aspiration in Swine" by Solomon et al. (CHEST, November 1998), which is incorporated herein by reference, describes a study to determine the feasibility of using real-time bronchoscope position technology coupled with previously acquired three-dimensional CT data to enhance transbronchial needle aspiration (TBNA). Eight swine were given percutaneously created target lesions for TBNA. A miniature position sensor was placed at the tip of a bronchoscope, and real-time position information during bronchoscopy was presented on a monitor simultaneously displaying previously acquired three-dimensional CT data. Ten to twenty metallic nipple markers, 1 mm wide, were secured on the animals' anterior chest wall for later image registration. The position sensor was touched to approximately four metallic nipple markers to register the animal's chest with the CT images. The authors conclude that real-time bronchoscope position technology coupled with previously acquired CT images may aid with TBNA of nonvisible extrabronchial lesions.

U.S. Pat. No. 5,636,255 to Ellis, which is incorporated herein by reference, describes a method and system for correlating accuracy of computer tomography (CT) image resolution. Small radio-opaque markers having a diameter less than one slice width of a CT scan are embedded in the object, such as a bony skeletal member, to be measured, and the object is then CT scanned so that the radio-opaque markers appear in at least two slices of the scan. The markers are also physically located by detecting them with a sensor, such as a positioning pointer. Also described is one form of marker comprising a tantalum sphere mounted in a ceramic, preferably alumina, pin.

U.S. Pat. No. 5,729,129 to Acker, which is incorporated herein by reference, describes a system for locating objects in space, such as medical instruments within the body of a patient, based upon transmission of magnetic fields from coils in a fixed frame of reference to sensors on the object or vice versa. The current supplied to the coils is described as being adjusted to assure that the sensors receive fields within a preselected range of magnitudes regardless of the location of the object in space. This is described as assuring that the sensor operates within its optimum range, and permits use of compact transmitters and sensors.

U.S. Pat. No. 5,873,822 to Ferre et al., which is incorporated herein by reference, describes a system for monitoring the position of a medical instrument with respect to a patient's body and for displaying at least one of a plurality of prerecorded images of said body responsive to the position of said medical instrument.

U.S. Pat. No. 5,902,239 to Buurman, which is incorporated herein by reference, describes an image guided surgery system including a position detection system which has a camera unit and which measures positions of markers on the patient and of a surgical instrument. The image guided surgery system also includes a transformation unit which automatically derives the mapping associated with imaging of the patient. The imaging is described as being performed, for example, by way of x-ray computed tomography or magnetic resonance imaging. The transformation unit is described as being arranged to match positions on the patient to positions in the image. To that end, the transformation unit is described as computing the minimum of a cost function.

Separately, the use of natural markers for registration purposes is described in an article entitled "3D CT-Guided Bronchoscopy with Real-Time Electromagnetic Position Sensor" by Solomon et al. (CHEST, December 2000), which is incorporated herein by reference. The article describes a study to compare two different image registration methods for accurately displaying the position of a flexible bronchoscope on a previously acquired three-dimensional CT scan during bronchoscopy. A miniature electromagnetic position sensor was placed at the tip of a flexible bronchoscope. Previously acquired three-dimensional CT scans were registered with the patient in the bronchoscopy suite. Registration method 1 used multiple skin fiducial markers. Registration method 2 used the inner surface of the trachea itself for registration. Method 1 was objectively assessed by measuring the error in distance between the real skin marker position and the computer display position. Methods 1 and 2 were assessed by the bronchoscopist correlating visual bronchoscopic anatomic location with the computer display position on the CT image. In accordance with method 2, a sensor at the scope tip was brought to the origin of the right upper lobe bronchus, then to the carina, and finally to the origin of the left upper lobe bronchus. At each of these anatomic points, the corresponding CT position was indicated to the computer. After these anatomic approximations, the sensor was dragged along the anterior and lateral walls of the trachea. The computer accepted approximately 30 of these wall points to form an approximation of the trachea position.

superDimension, Ltd. (Herzliya, Israel) has presented its superDimension/Bronchus system which uses the main bifurcations in the bronchial tree as natural anatomical landmarks for point-by-point image registration. Those bifurcations are marked in the CT data and later touched under endoscopic vision by a probe comprising an electromagnetic location sensor.

U.S. Pat. No. 6,782,287 to Grzeszczuk et al., which is incorporated herein by reference, describes a method and apparatus for tracking a medical instrument, as it is moved in an operating space to a patient target site in the space, by constructing a composite, 3-D rendition of at least a part of the operating space based on an algorithm that registers pre-operative 3-D diagnostic scans of the operating space with real-time, stereo x-ray or radiograph images of the operating space.

U.S. Pat. No. 6,892,090 to Verard et al., which is incorporated herein by reference, describes a surgical instrument navigation system that visually simulates a virtual volumetric scene of a body cavity of a patient from a point of view of a surgical instrument residing in the cavity of the patient. The surgical instrument navigation system includes: a surgical instrument; an imaging device which is operable to capture scan data representative of an internal region of interest within a given patient; a tracking subsystem that employs electromagnetic sensing to capture in real-time position data indicative of the position of the surgical instrument; a data processor which is operable to render a volumetric, perspective image of the internal region of interest from a point of view of the surgical instrument; and a display which is operable to display the volumetric perspective image of the patient.

An article entitled "Computed Tomographic Colography and Virtual Colonoscopy" by Ahlquist et al., (Gastrointestinal Endoscopy Clinics of North America, July 1997, pp 439-452), which is incorporated herein by reference, describes CT colography (CTC) as being a powerful new approach for imaging the colorectum, and a promising screening tool for the detection of colorectal neoplasia. From data generated by a helical CT scan, CTC uses virtual reality technology to produce highly discriminant two- and three-dimensional images that permit a thorough and minimally invasive evaluation of the entire colorectum. A dynamic CTC display technique from the endoluminal perspective, called "virtual colonoscopy," simulates colonoscopy by "flying" through the three-dimensional colon image. CTC is described as offering potential advantages in diagnostic performance, safety, and patient acceptance over current screening approaches. The authors state that although early data suggest excellent colorectal polyp detection rates, this nascent technology will require rigorous clinical investigation and further refinements to assess adequately its place in the endoscopist's armamentarium.

U.S. Pat. No. 5,920,319 to Vining et al., which is incorporated herein by reference, describes a computer system and a computer-implemented method for interactively displaying a three-dimensional rendering of a structure having a lumen and for indicating regions of abnormal wall structure.

An article entitled "A Virtual Bronchoscopic Navigation System for Pulmonary Peripheral Lesions" by Asano et al. (CHEST, 2006, 130:559-556), which is incorporated herein by reference, describes a study in which ultrathin bronchoscopy was performed for pulmonary peripheral lesions using a system that displays virtual bronchoscopy (VB) images of the lesion simultaneously with actual images, and navigates the bronchoscope to the target bronchus.

Software packages enabling the construction from CT data, and the subsequent viewing, of virtual endoscopy are available from multiple vendors. Such packages include, among others, the OsiriX Advanced Open-Source PACS Workstation DICOM Viewer which is a freeware, the General Electric Navigator (GE Medical Systems, Milwaukee, Wis., USA), the Vital Images Voxel View (Vital Images, Fairfield, Conn., USA), and the Voyager software (Phillips Medical Systems, Andover, Mass., USA).

U.S. Pat. No. 6,016,439 to Acker, which is incorporated herein by reference, describes a method and apparatus for synthetic view point imaging, the apparatus including an instrument insertable into the body of a patient. Using tissue image information defining an image of the patient's body, and defining the position of the distal end of the instrument within the body, synthetic images of the patient's body are synthesized having a viewpoint with a defined spatial relationship to the distal end of the instrument based on the image information and the determined position of the instrument.

US Patent Application Publication 2007/0015997 to Higgins et al., which is incorporated herein by reference, describes a method for providing guidance to the physician during a live bronchoscopy or other endoscopic procedures. The 3D motion of the bronchoscope is estimated using a fast coarse tracking step followed by a fine registration step. The tracking is based on finding a set of corresponding feature points across a plurality of consecutive bronchoscopic video frames, then estimating the new pose of the bronchoscope. A preferred embodiment is described in which the pose estimation is based on linearization of a rotation matrix. By giving a set of corresponding points across the current bronchoscopic video image, and the CT-based virtual image as an input, the same method is described as also being used for manual registration. The fine registration step is preferably a gradient-based Gauss-Newton method that maximizes the correlation between the bronchoscopic video image and the CT-based virtual image. The continuous guidance is described as being provided by estimating the 3D motion of the bronchoscope in a loop. Since depth-map information is available, tracking is described as being done by solving a 3D-2D pose estimation problem.

US Patent Application Publication 2007/0293721 to Gilboa, which is incorporated herein by reference, describes systems and methods employing a small gauge steerable catheter including a locatable guide with a sheath, particularly as an enhancement to a bronchoscope. A typical procedure is described as follows: The location of a target in a reference coordinate system is detected or imported. The catheter is navigated to the target which tracking the distal tip of the guide in the reference coordinate system. Insertion of the catheter is typically via a working channel of a conventional bronchoscope. Once the tip of the catheter is positioned at the target, the guide is withdrawn, leaving the sheath secured in place. The sheath is then used as a guide channel to direct a medical tool to the target.

US Patent Application Publication 2007/0276180 to Greenburg et al., which is incorporated herein by reference, describes a clip or flexible handle extension which facilitate simultaneous retention and operation of a bronchoscope and associated bronchoscopic tools held in one hand to allow operation by a single practitioner. Also described is an adapter for the connection port of the working channel of a bronchoscope, which performs both sealing and tool-locking functions. Also described is a guide sheath arrangement with a reduced-flexibility proximal portion, to facilitate insertion of tools into the guide sheath.

US Patent Application Publication 2007/0225559 to Clerc et al., which is incorporated herein by reference, describes a visualization system including a small gauge vision catheter that is designed to be stand-alone or received within an instrument channel of a larger endoscope. The vision catheter has imaging means disposable within an imaging channel, a working channel, and an electromagnetic sensor element insertable into the working channel of the catheter to provide position tracking. The working channel of the catheter also provides access for therapeutic and diagnostic tools.

US Patent Application 2006/0076023 to Rapacki et al., which is incorporated herein by reference, describes a flow control device which includes a sealing component that can be positioned within a bronchial lumen. The sealing component can comprise two or more overlapping segments that are movable relative to one another such that the segments collectively form a seal that can expand and contract in size to fit within and seal bronchial lumens of various sizes.

U.S. Pat. No. 6,592,520 to Peszynski et al., which is incorporated herein by reference, describes an intravascular ultrasound imaging apparatus and method. The ultrasound system includes an intravascular catheter with an ultrasound transducer array, a transmit beamformer, a receive beamformer, and an image generator. The intravascular catheter has an elongated body made for insertion into a blood vessel and connected to a catheter handle. The catheter includes a catheter core located inside a steerable guide sheath, both having a proximal part and a distal part. The catheter includes an articulation region connected to a positioning device for positioning the transducer array to have a selected orientation relative to an examined tissue region.

An article entitled "Multimodality Bronchoscopic Diagnosis of Peripheral Lung Lesions: A Randomized Controlled Trial," by Eberhardt et al. (American Journal of Respiratory and Critical Care Medicine Vol 176. pp. 36-41, 2007), which is incorporated herein by reference, describes a trial in which endobronchial ultrasound (EBUS) and electromagnetic navigation bronchoscopy (ENB), and a combination of these modalities, were used for bronchoscopic diagnosis of peripheral lung lesions. The authors conclude that the combined EBUS and ENB improves the diagnostic yield of flexible bronchoscopy in peripheral lung lesions without compromising safety.

An article entitled, "Electromagnetic Navigation during Flexible Bronchoscopy," by Schwartz et al. (Respiration 2003; 70:516-522), which is incorporated herein by reference, describes a study to determine the practicality, accuracy and safety of real-time electromagnetic navigation, coupled with previously acquired 3D CT images, in locating artificially created peripheral lung lesions in a swine model. The authors conclude that real-time electromagnetic positioning technology coupled with previously acquired CT images is an accurate technology added to standard bronchoscopy to assist in reaching peripheral lung lesions and performing biopsies.

An article entitled "Electromagnetic Catheter Navigation During Bronchoscopy," by Hautmann et al. (Chest. 2005; 128:382-387), which is incorporated herein by reference, describes a study to assess the usability, accuracy, and safety of electromagnetic navigation during flexible bronchoscopy in a clinical setting. The article describes the navigation as having been performed using an electromagnetic tracking system with a position sensor encapsulated in the tip of a flexible catheter that was pushed through the working channel of the bronchoscope. Real-time, multiplanar reconstruction of a previously acquired CT data set provided three-dimensional views for localization of the catheter. To match the position of the sensor with the CT scan, four anatomic landmarks were used for registration. The sensor position generated in the navigation system was controlled by fluoroscopy, and the corresponding error distances were measured. This was performed with all solitary pulmonary nodules and at two different peripheral locations of the right upper lobe (RUL).

The following patents and patent applications, which may be of interest, are incorporated herein by reference:

U.S. Pat. No. 6,836,745 to Seiler et al
U.S. Pat. No. 5,744,953 to Hansen
U.S. Pat. No. 4,849,692 to Blood U.S. Pat. No. 6,445,943 to Ferre et al.
U.S. Pat. No. 6,784,660 to Ashe
U.S. Pat. No. 6,990,427 to Kirsch et al.
U.S. Pat. No. 6,783,536 to Vilsmeier et al.
U.S. Pat. No. 6,947,788 to Gilboa et al.
U.S. Pat. No. 4,017,858 to Kuypers
U.S. Pat. No. 6,636,757 to Jascob et al.
U.S. Pat. No. 5,697,377 to Wittkampf
U.S. Pat. No. 6,490,474 to Willis et al.
U.S. Pat. No. 3,470,876 to Barchilon
US Patent Application Publication 2006/0173291 to Glossop
US Patent Application Publication 2007/0055090 to Neustadter et al.
US Patent Application Publication 2007/0205373 to Komblau et al.

The following companies manufacture location sensors and/or image-guided navigation systems that comprise magnetic technologies:
MediGuide Ltd. (Haifa, Israel);
Biosense Webster Inc. (Diamond Bar, Calif., USA);
Northern Digital Inc. (Waterloo, Canada);
BrainLAB AG (Kirchheim/Heimstetten, Germany);
Ascension Technology Corporation (Burlington, Vt., USA)

The following companies manufacture location sensors and/or image-guided navigation systems that comprise electromagnetic technologies:
superDimension Ltd. (Herzliya, Israel);
Polhemus Navigation Sciences, Inc. (Burlington, Vt., USA);
Surgical Navigation Technologies, Inc. (Louisville, Colo., USA);
Medtronic Navigation (Louisville, Colo., USA);
Traxtal Technologies (Toronto, Canada);

The following company manufactures location sensors and/or image-guided navigation systems that comprise radiation-sensing technologies:
NavoTek, Ltd., also known as VasTrack, Ltd., (Yokne'am, Israel)

The following company manufactures magnetically-maneuverable medical tools:
Sterotaxis, Inc. of St. Louis. (MO, USA)

Location sensors comprising a longitudinal coil and having an outer diameter of approximately 0.25 mm to 0.3 mm were presented by:
MediGuide, Ltd. (Haifa, Israel) at the Innovations in Cardiovascular Interventions meeting held in Tel Aviv, Israel on Dec. 3 and 4, 2006, and
Ascension Technologies, Inc., (Burlington, Vt., USA) at the Trans Catheter Therapeutics conference and exhibition held in Washington D.C., USA on Oct. 22-24, 2007

Olympus America, Inc. manufactures an endo-bronchial ultrasound probe (EBUS)

Boston Scientific and Volcano manufacture intra-vascular ultrasound probes (IVUS)

TopSpin Medical (Lod, Israel) manufactures an intra-vascular MRI probe (IVMRI)

Vida Diagnostics (Iowa City, Iowa, USA) manufactures the Emphysema Profiler and the Pulmonary Workstation.

DeepBreeze, Ltd. (Or Akiva, Israel) manufactures a Vibration Response Imaging system.

All of the above-listed references are incorporated herein by reference.

SUMMARY OF THE CURRENT INVENTION

In some embodiments of the present invention, devices and methods are used for performing medical procedures in tree-like luminal structures within a subject's body, typically using an image-guided navigation system. In some embodiments, such procedures comprise at least some of the following elements:
(i) Acquiring images from one or more sources. Typically, but not always, the images are pre-procedure.
(ii) Observing and interpreting the images. In some cases, also making note of desired locations to diagnose and/or treat.
(iii) Registering the images to the current position of the patient's body via a "tree-to-tree" registration process. Typically the images are registered to the body's current position by registering (a) lines along two or more branching lines of the tree-like luminal structure as viewed within the pre-procedure image, with (b) the intra-procedure location of the two or more branching lines of the tree-like luminal structure within the subject's body. Typically, two or more branching lines that are spaced from each other are selected as the two or more branching lines. The inventor hypothesizes that the described tree-to-tree registration, when performed in a multi-lumen structure, typically provides higher accuracy compared with traditional registration methods which typically rely on discrete fiducials and/or a single line or path.
(iv) Co-registering intra-procedure images with the aforementioned pre-procedure images, such that image frames of the intra-procedure images are matched with locations within the intra-procedure images.
(v) Inserting a maneuverable and localizable sheath into the luminal structure. In some embodiments, the sheath is inserted through an endoscope, and typically beyond the endoscope's own reach.
(vi) Inserting medical tools through one or more lumens of that sheath.
(vii) Navigating the medical tools to desired locations concurrently with the localizable sheath, and with their current location being superimposed on the registered pre-procedure images.
(viii) Co-utilizing intra-procedure imaging together with the aforementioned registered pre-procedure images for performing ongoing corrections to the initial registration of those images to the patient's body. Such ongoing corrections are of particular use in moving luminal structures, and typically contribute to higher navigational accuracy.
(ix) Co-utilizing intra-procedure imaging together with the aforementioned pre-procedure images for providing additional clinical information at the current locations of the navigated medical tools.
(x) Determining the arrival of navigated tools at desired locations when superimposed on the previously-registered pre-procedure images.
(xi) Utilizing the intra-procedure imaging for verifying the arrival of navigated tools at the desired locations. In some embodiments, verification contributes to higher navigational accuracy.
(xii) Utilizing the tools at the desired locations.

In some embodiments, some of the aforementioned elements are repeated, combined and/or performed in a sequence that differs from the above.

There is therefore provided, in accordance with an embodiment of the present invention, registration apparatus for use with an imaging device configured to acquire a pre-procedure image of a portion of a body of a subject while the portion is at a pre-procedure position, and a display configured to display the pre-procedure image, the apparatus including:

an input unit configured to receive, as an input from a user, an indication of two or more lines within the pre-procedure image of the portion that correspond to respective branches of a multi-branch luminal structure;

a probe configured to move within the portion along two or more lines in the multi-branch luminal structure that respectively correspond to the two or more lines within the pre-procedure image;

a location sensor coupled to the probe and configured to sense location coordinates along the two or more lines along which the probe moves, while the portion is at a current position; and a control unit configured to register the pre-procedure image of the portion with the current position of the portion by registering (a) the two or more lines within the pre-procedure image, with (b) the location coordinates along the two or more lines.

In an embodiment, the control unit is configured to receive the input from the user via use by the user of virtual endoscopy.

In an embodiment, the control unit is configured to register (a) with (b) according to a best-fit algorithm.

In an embodiment, the two or more lines along which the probe moves include two or more lines in a location selected from the group consisting of: a bronchial tract of the subject, a biliary tract of the subject, and coronary vessels of the subject, and the location sensor is configured to sense location coordinates along the two or more lines in the selected location.

In an embodiment, the two or more lines along which the probe moves directly branch from a common bifurcation point of the multi-branch luminal structure, and the location sensor is configured to sense location coordinates along the two or more lines that branch from the common bifurcation point.

In an embodiment, in registering (a) with (b), the control unit is configured to assign a first relative weighting to a first one of the two or more lines along which the probe moves, and a second relative weighting to a second one of the two or more lines along which the probe moves.

In an embodiment, in registering (a) with (b), the control unit is configured to assign a first relative weighting to respective first portions of respective lines of the two or more lines along which the probe moves, and a second relative weighting to respective second portions of the respective lines of the two or more lines along which the probe moves.

In an embodiment, the location sensor is configured to gate the sensing of the location coordinates to a given phase of a cyclic physiological cycle that the portion of the subject's body undergoes.

In an embodiment, the pre-procedure image is acquired during the given phase, and the control unit is configured to register (a) with (b) by registering (a) the two or more lines within the pre-procedure image acquired during the given phase, with (b) the location coordinates along the two or more lines.

In an embodiment, the control unit is configured to register (c) a region within the pre-procedure image that corresponds to a region of the subject's body that is distal to the two or more lines along which the probe moves, with (d) the region of the subject's body, by registering (a) with (b).

In an embodiment, the region includes a region of the subject's body that is distal to an occlusion, and the control unit is configured to register (c) with (d) by registering:

(e) two or more lines within the pre-procedure image that correspond to two or more lines along which the probe moves that are proximal to the occlusion, with (f) location coordinates along the two or more lines along which the probe moves that are proximal to the occlusion.

In an embodiment, the region includes a region of a respiratory tract of the subject that is distal to major airways of the subject's respiratory tract, the two or more lines along which the probe moves include two or more major airways of the subject's respiratory tract, and the control unit is configured to register (c) with (d) by registering (e) two or more lines within the image of the portion of the subject's body that correspond to the two or more major airways, with (f) location coordinates along the two or more major airways.

There is additionally provided, in accordance with an embodiment of the invention, apparatus for use with a medical tool, and a first location sensor configured to detect a location of the tool, the apparatus including:

a first imaging device configured to acquire an image of a portion of a body of a subject;

a second imaging device configured to acquire an image of a region within the portion, while the second imaging device is disposed at a location within the portion; and a control unit configured:

to identify a correspondence between (a) the image of the region acquired by the second imaging device, and (b) a derived location within the image acquired by the first imaging device that corresponds to the location of the second imaging device, to store (a) the image of the region acquired by the second imaging device and (b) the derived location within the image acquired by the first imaging device, based on the identified correspondence, to receive from the first location sensor an indication that the medical tool is in a vicinity of the derived location, to retrieve from storage the image of the region acquired by the second device, at a time when the second imaging device is not at the derived location, and when the second imaging device is not at the derived location and the medical tool is in the vicinity of the derived location, to display (a) the image acquired by the first imaging device with an indication of the derived location, and (b) the retrieved image of the region acquired by the second imaging device.

In an embodiment, the control unit is configured to display the image acquired by the first imaging device and the retrieved image of the region acquired by the second imaging device in a virtual endoscopy format.

In an embodiment, in displaying the image acquired by the first imaging device and the retrieved image of the region acquired by the second imaging device, the control unit is configured to fuse the image acquired by the first imaging device and the retrieved image of the region acquired by the second imaging device.

In an embodiment, the apparatus further includes a second location sensor coupled to the second imaging device and configured to detect location coordinates of the second imaging device, while the second imaging device is disposed at the location within the portion, the first imaging device is configured to acquire the image of the portion before the second imaging device acquires the image of the region, and the control unit is configured to identify the correspondence between (a) and (b) by registering the derived location within the image acquired by the first imaging device that corresponds to the location of the second imaging device, with the location coordinates of the second imaging device.

In an embodiment,
the control unit is configured to receive an indication of location coordinates of the second imaging device, while the second imaging device is disposed at the location within the portion,
the first imaging device is configured to acquire the image of the portion before the second imaging device acquires the image of the region, and the control unit is configured to register the correspondence between (a) and (b) by registering the derived location within the image acquired by the first imaging device that corresponds to the location of the second imaging device, with the location coordinates of the second imaging device.

In an embodiment,
the first imaging device is configured to acquire the image of the portion at a time that the second imaging device acquires the image of the region, and
the control unit is configured to identify the correspondence between (a) and (b) by image processing the image of the portion acquired by the first imaging device to determine the location of the second imaging device.

In an embodiment, the first imaging device includes an imaging device selected from the group consisting of: a CT scanner and a fluoroscope.

In an embodiment, the second imaging device includes an intraluminal imaging device selected from the group consisting of: an intraluminal ultrasound probe, an intraluminal optical-coherence-tomography probe, and an intraluminal MRI probe.

There is additionally provided, in accordance with an embodiment of the invention, apparatus for use with a first imaging device configured to acquire a pre-procedure image of a portion of a body of a subject while the portion is at a pre-procedure position, and a display configured to display the acquired image, the apparatus including:
a probe configured to move to a plurality of locations within the portion;
a location sensor coupled to the probe and configured to sense location coordinates of respective locations of the location sensor when the location sensor is at the plurality of locations, while the portion is at a current position;
a second imaging device coupled to the probe and configured to acquire a set of images of regions within the portion, respective images of the set being acquired while the probe is disposed at the respective locations; and
a control unit configured to:
register the pre-procedure image of the portion with the current position of the portion, by registering (a) respective locations within the pre-procedure image that correspond to the respective locations of the location sensor, with (b) the respective locations of the location sensor, and
register (a) respective locations within the pre-procedure image that correspond to the respective locations of the location sensor, with (b) respective images from the set of images that were acquired by the second imaging device while the location sensor was disposed at the respective locations of the location sensor.

In an embodiment,
the apparatus further includes a medical tool configured to perform a function with respect to the portion,
the probe includes a sheath, the sheath shaped to define a sheath channel, and the tool is configured to be inserted into the portion via the sheath channel.

In an embodiment,
the probe includes a sheath, the sheath shaped to define a sheath channel, and the second imaging device is configured to be inserted into the portion via the sheath channel.

There is further provided, in accordance with an embodiment of the invention, apparatus for use with (a) an airway of a subject, the airway leading to a region suffering from pulmonary disease, (b) an imaging device configured to acquire a pre-procedure image of a portion of the subject's body that includes at least a portion of the region, and (c) a display configured to display the acquired image, the apparatus including:
a plug configured to be placed in the airway, the plug defining an opening therethrough that is in an open state thereof when something is inserted through the opening and is in a closed state thereof when nothing is inserted through the opening;
a tool having a distal portion configured to be inserted through the opening to a site distal to the plug and to facilitate suctioning therethrough of fluid, the fluid being disposed within the region and distal to the plug; and
a location sensor coupled to the distal portion of the tool, configured (a) to sense a location of the distal portion of the tool when the distal portion of the tool is at the site distal to the plug and (b) to facilitate location of the distal portion of the tool in the acquired image.

In an embodiment, the tool includes a sheath and the location sensor is attached to the sheath.

In an embodiment, the apparatus further includes an endoscope configured to be inserted into the airway, the endoscope being unable to be inserted through the opening, and the tool is configured to be inserted through the opening by protruding from a distal end of the endoscope.

In an embodiment, the apparatus further includes a sheath, and the tool is configured to be inserted through the sheath.

In an embodiment, the location sensor is attached to the distal portion of the tool.

In an embodiment, the location sensor is coupled to the distal portion of the tool via the sheath.

In an embodiment, the location sensor is attached to the sheath.

In an embodiment, the apparatus includes a control unit configured to:
register the pre-procedure image of the portion with a current position of the portion, and
generate an indication of the distal portion of the tool at a location within the registered image that corresponds to the sensed location of the distal portion of the tool.

In an embodiment,
the tool is configured to be moved along a plurality of lines within the portion,
the location sensor is configured to sense location coordinates along two or more lines along which the tool moves, while the portion is at a current position, and
the control unit is configured:
to register the pre-procedure image of the portion with the current position of the portion,
by registering (c) two or more lines within the pre-procedure image that correspond to the two or more lines along which the tool moves, with (d) the location coordinates along the two or more lines along which the tool moves.

In an embodiment, the tool is configured to be directed toward respective single bullae of the region, and to facilitate suctioning through the tool of fluid from within the respective single bullae.

In an embodiment, the apparatus further includes:
a sheath, the tool being configured to be inserted through the sheath; and
an endoluminal imaging probe configured to be inserted through the sheath and to facilitate verification of a location of the sheath with respect to the respective bullae.

In an embodiment, the tool is configured to suction fluid from within each of the single bullae a plurality of times.

There is additionally provided, in accordance with an embodiment of the invention, apparatus for use with a first imaging device configured to acquire a pre-procedure image of a portion of a body of a subject, and a display configured to display the acquired image, the apparatus including:
a sheath configured to be inserted into the portion of the subject's body, the sheath having a body that defines a main channel therethrough;
a tool configured to be inserted into the portion of the subject's body via the main channel;
a location sensor disposed within the body of the sheath and configured to sense a location of a distal portion of the sheath; and
a control unit configured to generate an indication of the location of the distal portion of the sheath with respect to the acquired image of the portion of the subject's body.

In an embodiment, the location sensor includes one or more particles of a radiating substance coupled to the sheath.

In an embodiment, the location sensor includes a plurality of location sensors disposed along the distal portion of the sheath, within the body of the sheath.

In an embodiment, the portion includes a lung of the subject, and the tool is configured to facilitate a procedure selected from the group consisting of: diagnosing a lesion of the lung and treating a lesion of the lung.

In an embodiment, the portion includes a bronchial tract of the subject, and the tool is configured to facilitate a transbronchial lymph node aspiration procedure.

In an embodiment, the portion includes a heart of the subject, and the tool is configured to facilitate a left side lead placement procedure with respect to the subject's heart.

In an embodiment, the portion includes a biliary tract of the subject, and the tool is configured to facilitate a procedure with respect to the subject's biliary tract.

In an embodiment, the apparatus further includes an imaging device configured to:
be inserted into the portion via the main channel of the sheath, and
acquire images of regions within the portion while the imaging device is disposed within the portion.

In an embodiment, an outer diameter of the sheath is less than 2.8 mm.

In an embodiment, an inner diameter of the main channel of the sheath is greater than 1.2 mm.

In an embodiment, the inner diameter of the main channel of the sheath is greater than 1.8 mm.

In an embodiment, the location sensor includes one or more coils oriented in a single direction.

In an embodiment, an outer diameter of each of the one or more coils is less than 0.3 mm.

In an embodiment, the control unit is configured to generate an indication, on the display of the acquired image, of a location of a distal portion of the tool.

In an embodiment, the control unit is configured to determine the location of the distal portion of the tool based on an offset from the location of the distal portion of the sheath.

In an embodiment, the distal portion of the tool is configured to protrude from a distal end of the sheath by a fixed amount, and the control unit is configured to determine the location of the distal portion of the tool based on the fixed amount.

In an embodiment, the distal portion of the tool is configured to protrude from a distal end of the sheath by a measurable variable amount, and the control unit is configured to calculate the offset based on a measurement of the variable amount.

In an embodiment, the sheath includes a maneuverable sheath.

In an embodiment, the apparatus further includes steering wires disposed within the body of the sheath, and the sheath is configured to be maneuvered using the steering wires.

In an embodiment, the control unit is configured to:
register the pre-procedure image of the portion with a current position of the portion, and
generate an indication of the distal portion of the sheath at a location within the registered image that corresponds to the sensed location of the distal portion of the sheath.

In an embodiment,
the sheath is configured to be moved along a plurality of lines within the portion;
the location sensor is configured to sense location coordinates along two or more lines along which the sheath moves, while the portion is at the current position, and
the control unit is configured:
to register the pre-procedure image of the portion with the current position of the portion,
by registering (a) two or more lines within the pre-procedure image that correspond to the two or more lines along which the sheath moves, with (b) the location coordinates along the two or more lines.

In an embodiment,
the apparatus further includes an endoscope defining an endoscope channel therethrough and configured to be inserted toward the portion of the subject's body,
and at least a distal portion of the sheath is configured to be inserted, via the endoscope channel, (a) distal to a distal end of the endoscope and (b) into the portion of the subject's body.

In an embodiment, the distal portion of the sheath is configured to be advanced distal to a position beyond which the endoscope is unable to be advanced.

In an embodiment, the distal portion of the sheath is configured to be inserted into an airway of the subject having an inner diameter that is less than an outer diameter of the endoscope.

In an embodiment, the distal portion of the sheath is configured to be inserted into a duct of a biliary tract of the subject having a diameter that is less than an outer diameter of the endoscope.

In an embodiment, the distal portion of the sheath is configured to be inserted into a nasal passage of the subject having a diameter that is less than an outer diameter of the endoscope.

There is further provided, in accordance with an embodiment of the invention, a method for registering a pre-procedure image of a portion of a body of a subject with a current position of the portion and subsequently adjusting the registration, the method including:
identifying two or more image-fiducials within the pre-procedure image that correspond to respective body-fiducials within the portion;
detecting location coordinates of the respective body-fiducials within the portion;

registering the pre-procedure image with the current position of the portion by registering (a) respective image-fiducials that correspond to respective body-fiducials within the portion, with (b) the location coordinates of respective body-fiducials within the portion;

subsequent to the registering, acquiring, with an imaging device that is disposed at an imaging-location within the portion, an image of at least one landmark within the portion;

identifying the landmark within the pre-procedure image;

detecting location coordinates of the imaging device while the imaging device is disposed at the imaging-location; and adjusting the registration of the pre-procedure image of the portion with the current position of the portion, in response to the detected location coordinates of the imaging device.

In an embodiment, the at least one landmark includes at least one of the body-fiducials, and acquiring the image of the at least one landmark includes acquiring an image of the at least one of the body-fiducials.

In an embodiment, the at least one landmark includes at least one landmark that is not one of the body-fiducials, and acquiring the image of the at least one landmark includes acquiring an image of the at least one landmark that is not one of the body-fiducials.

The present invention will be more fully understood from the following detailed description of embodiments thereof, taken together with the drawings, in which:

BRIEF DESCRIPTIONS OF THE FIGURES

Figure 1B:
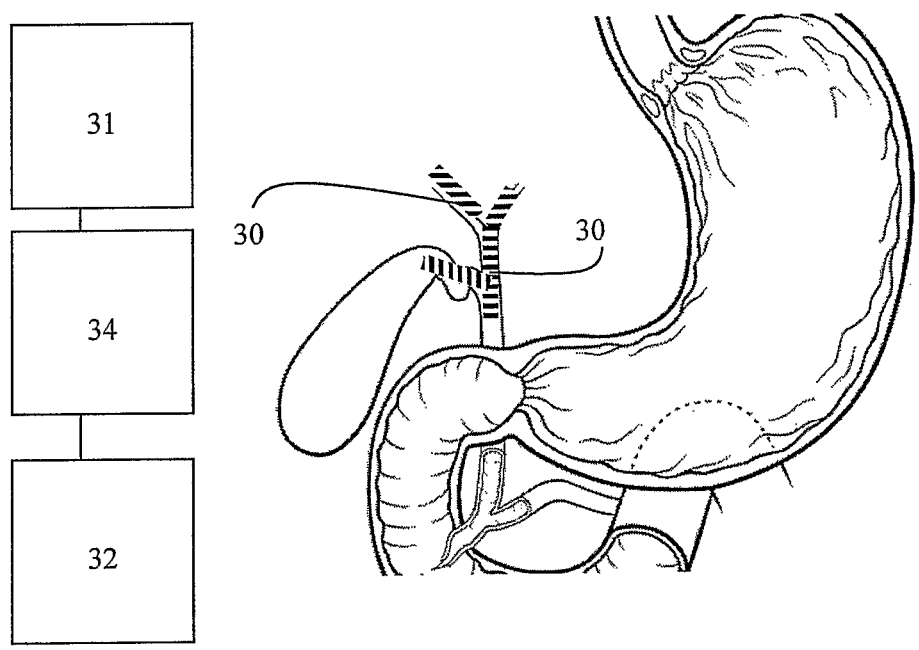
Figure 2:
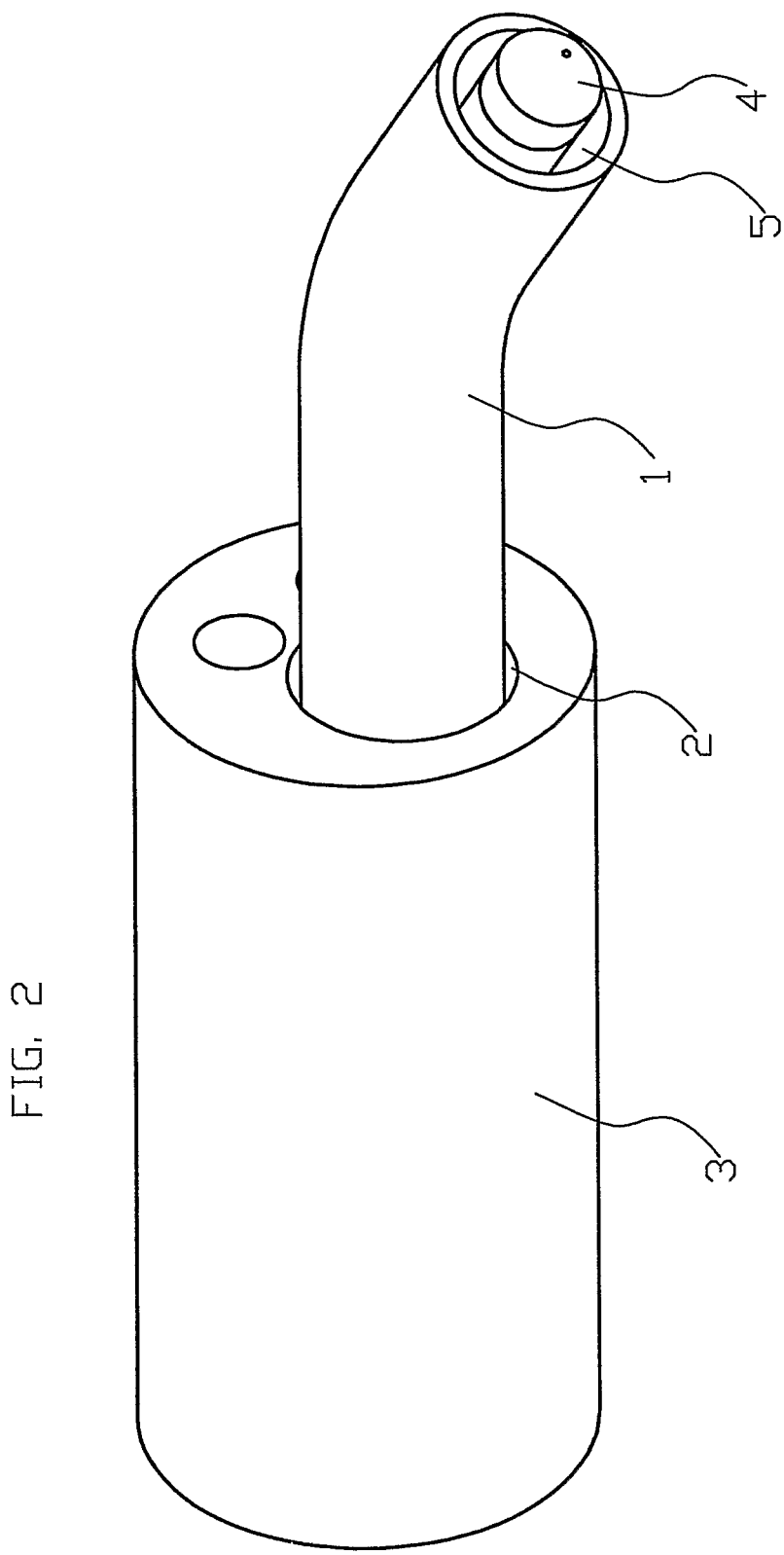
Figure 3:
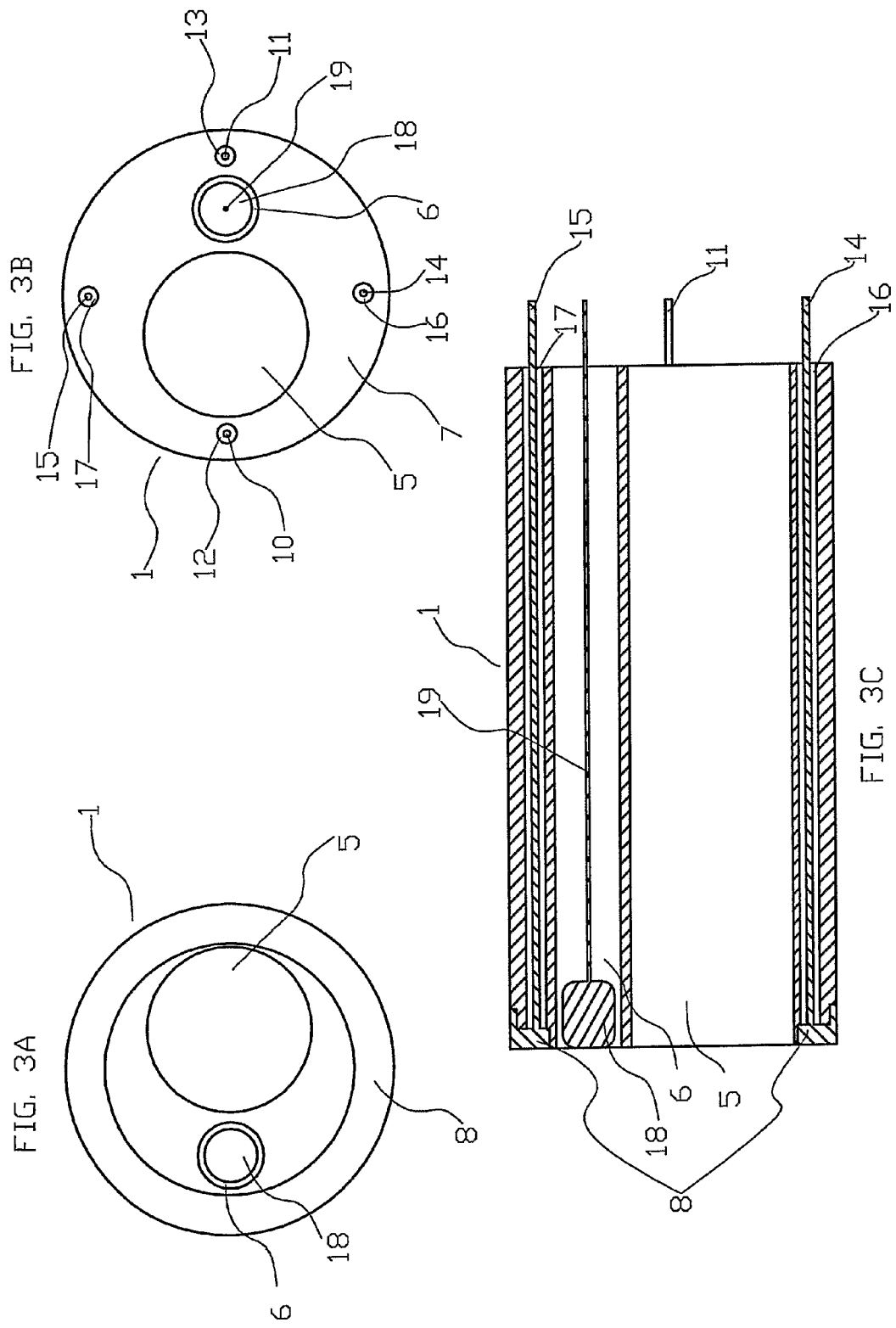
Figure 4:
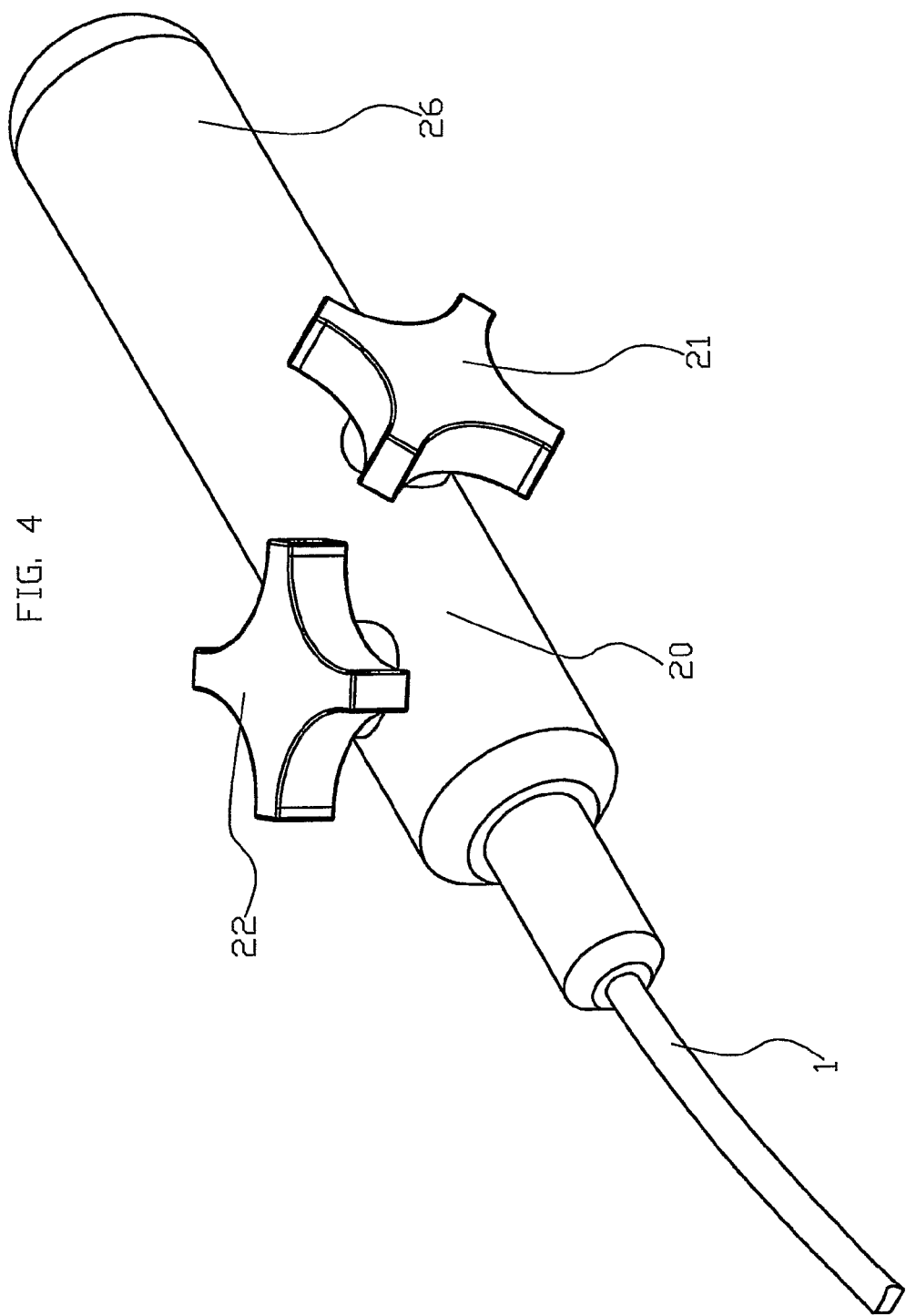
Figure 5:
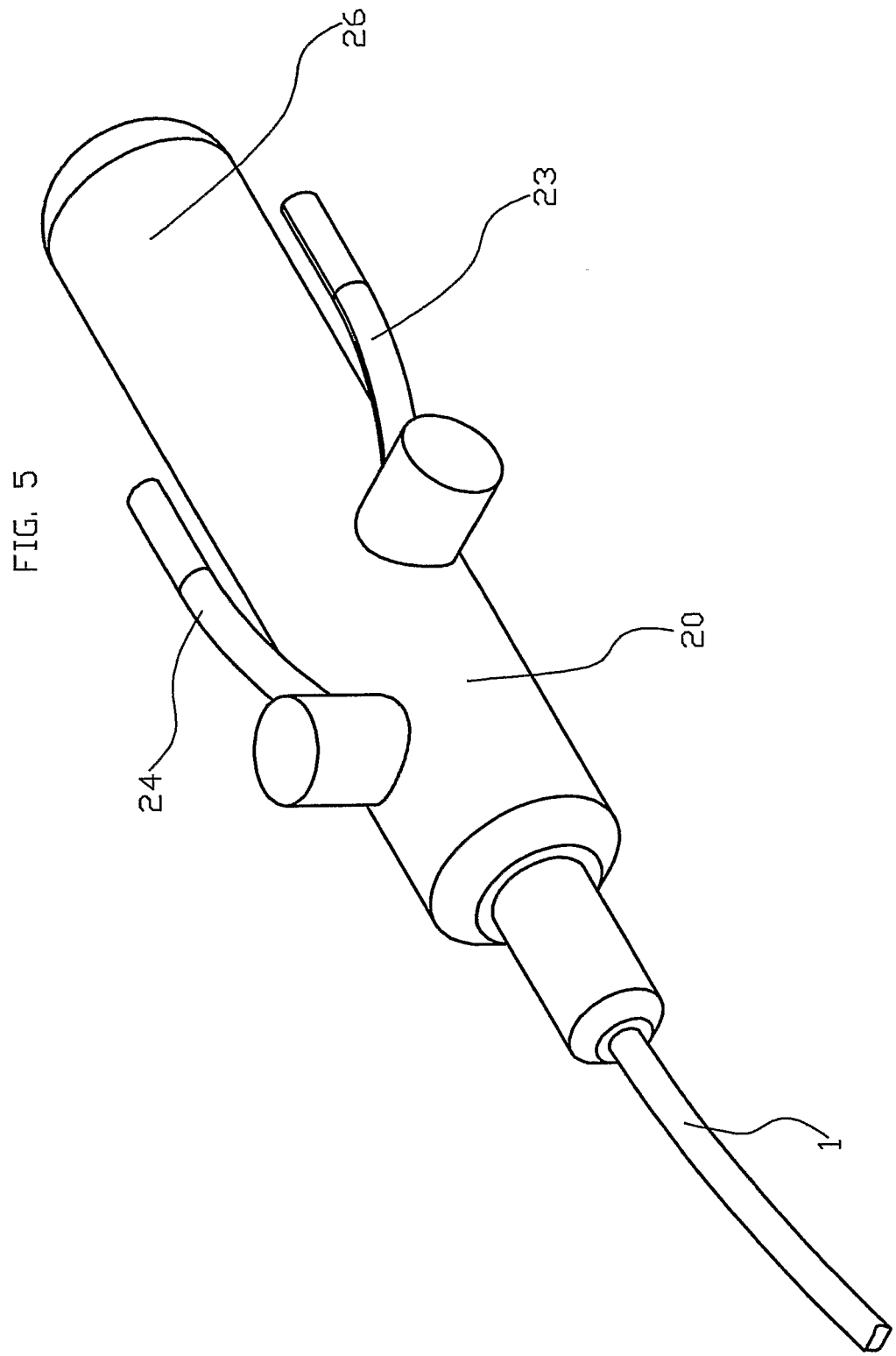
Figure 6:
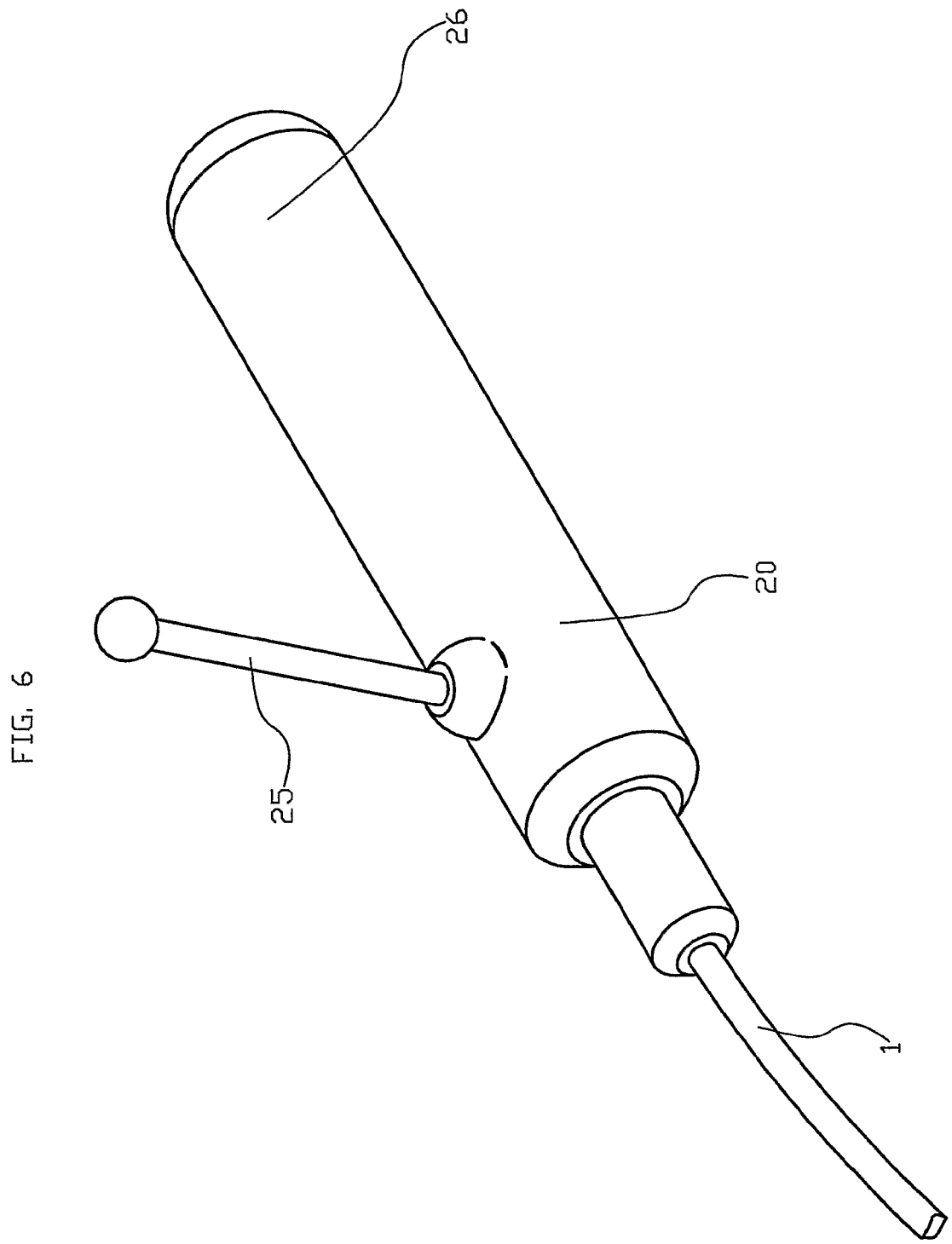
Figure 7:
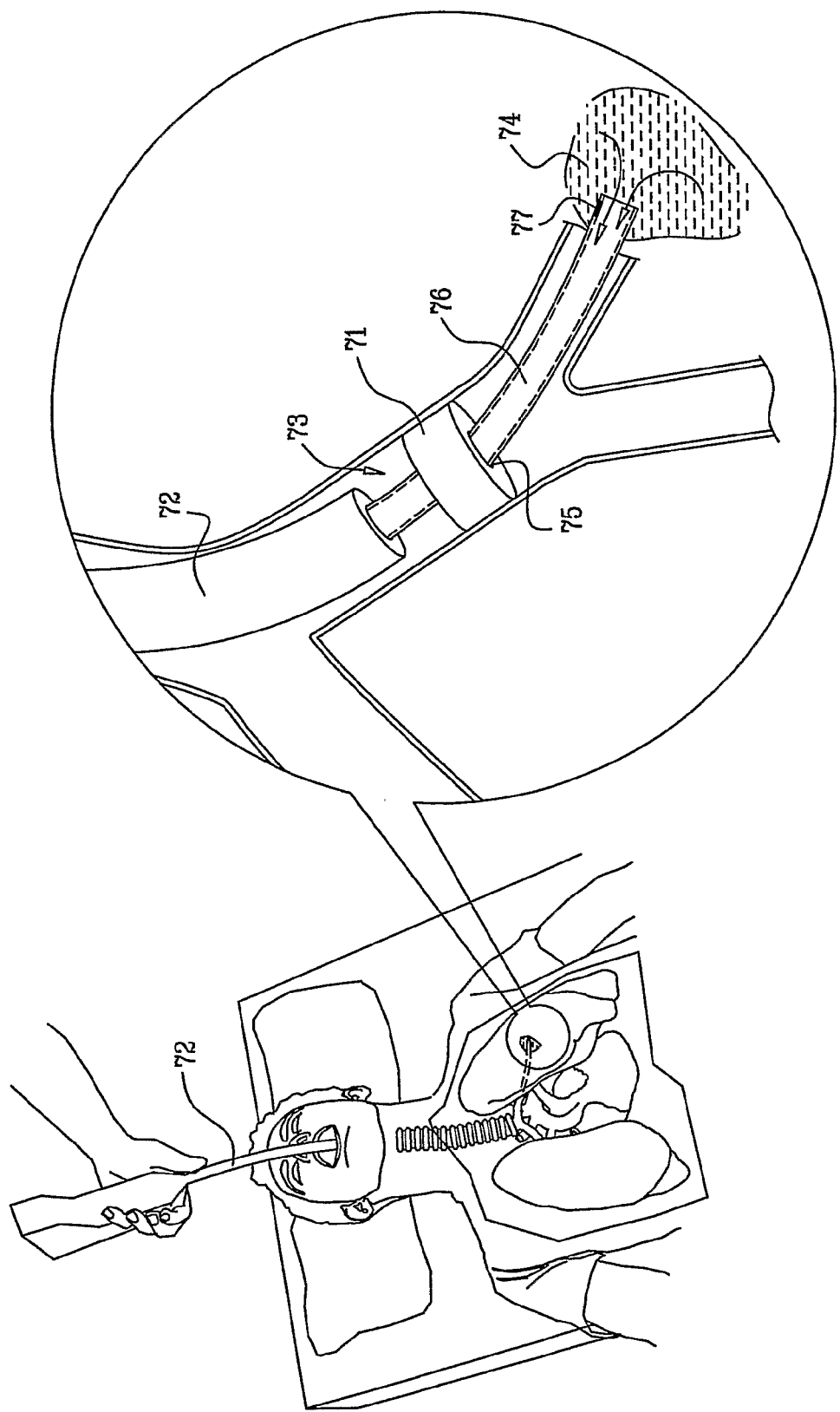

FIGS. 1A-B are schematic illustrations of tree-like luminal structures designated for imaging with a pre-procedure imaging device, in accordance with an embodiment of the present invention;

FIG. 2 is a schematic illustration of a maneuverable, localizable sheath inserted through the working channel of an endoscope, a tool being inserted through the main channel of the sheath, in accordance with an embodiment of the present invention;

FIGS. 3A-C are schematic illustrations of respective views of the maneuverable, localizable sheath of FIG. 2, in accordance with an embodiment of the present invention;

FIGS. 4-6 are schematic illustrations of respective embodiments of steering actuators for maneuverable sheaths, in accordance with respective embodiments of the present invention; and FIG. 7 is a schematic illustration of a maneuverable sheath being inserted through a plug and toward a region suffering from pulmonary disease, in accordance with an embodiment of the present invention.

DETAILED DESCRIPTION OF EMBODIMENTS OF THE CURRENT INVENTION

In some embodiments of the present invention, devices and methods are used for performing medical procedures in tree-like luminal structures by means of an image-guided navigation system. Although embodiments are described with respect to the tracheobronchial airways, the scope of the invention includes applying the described apparatus and methods to other tree-like luminal structures, such as the biliary tract and the duodenum, the coronary arteries and/or veins, the arterial and/or venous structures in the liver, and/or other arterial and/or venous structures. The scope of the invention additionally includes applying, as appropriate, some of the described apparatus and methods to other complex, multi-lumen tracts such as the nasal sinuses and the urinary tract.

A. Terminology

As used herein:

The terms 'tool,' 'probe,' 'medical tool,' and 'medical probe' all refer to any tool or probe that may be inserted into a body lumen. It may be any type of a diagnostic or therapeutic or other functional tool including, but not limited to, biopsy forceps, a biopsy brush, a biopsy needle, an aspiration needle, a "cork-screw-like" biopsy "excavator" device, a navigational probe, a localization probe, a probe comprising a location sensor, a tissue characterization probe, a leading tool, a guiding tool, a guide wire, a sheath, a tool for widening/penetrating/opening an occlusion, a tool for the analysis of the composition of fluid, a measurement probe, an electrophysiological probe, a stimulation tool, an electrocautery tool, an RF ablation tool, a cryoablation tool, an ultrasound ablation tool, a steam ablation tool, any other type of an ablation tool, a cryo biopsy tool, a drug or substance delivery tool, a chemotherapy tool, a photodynamic therapy tool, a brachytherapy tool, a local irradiation tool, a laser tool, a tool for delivering markers or biomarkers, a tool for delivering biological glue, a tool for delivering/placing/removing an endoluminal plug, a tool for delivering/placing/removing a stent, a tissue-contracting tool, a tool for delivering/placing/removing a balloon, a sensor, a tool for delivering/placing/removing a valve, a tool for delivering/placing/removing a graft, a tool for delivering/placing/removing a stent graft, a tool for delivering/placing/removing an inhaler or exhaler, an irrigation tool, a suction tool, a ventilation tool, a lavage tool, a surgical tool, a tool for delivering/placing/removing, a lead of an electrophysiological device, an electrophysiological mapping and/or sensing tool, a light source, an optical fiber, an imaging tool, or any combination thereof.

The temms 'image' or 'imaging' refer to imaging modalities and imaging devices utilized in medical procedures and comprising, among others: ionizing radiation, non-ionizing radiation, video, optical fiber, video endoscopy, fiber endoscopy, X-ray, fluoroscopy, angiography, ultrasound, Gamma camera imaging, CT, PET, PET-CT, CT angiography, SPECT, MRI, Optical Imaging, Optical Coherence Tomography (OCT), Vibration Response Imaging (VRI), electrical mapping imaging, infra-red imaging, other forms of functional imaging, or any combination or fusion thereof. Examples of ultrasound imaging devices include Endo-Bronchial Ultrasound (EBUS), Trans-Thoracic Echo (TTE), Trans-Esophageal Echo (TEE), Intra-Vascular Ultrasound (IVUS), Intra-Cardiac Ultrasound (ICE).

The terms 'proximal' or 'proximally' mean towards the point of entry of a medical tool into the body lumen, tract or cavity, while the terms 'distal' and 'distally' mean further away from the point of entry into the body lumen, tract or cavity.

The terms 'location,' 'localized,' and 'localizable,' where used in the context of determining the location of a tool or probe (or specifically of its distal tip), mean position along the X axis of a reference frame of coordinates, position along the Y axis of a reference frame of coordinates, position along the Z axis of a reference frame of coordinates, orientation in the roll angle, orientation in pitch angle, orientation in the yaw angle, or any combination thereof.

The term 'location sensor' refers to sensors producing information pertaining to the location of a tool, or specifically of the distal tip thereof, within a patient's body and typically while not requiring a direct line of sight to the outside of the patient's body. Such location sensors are typically part of an image-guided navigation system.

The terms 'navigation system' and 'image guided navigation system' refer to a navigation system which typically comprises at least some of the following elements: one or more location sensor(s) coupled to a tool being navigated; one or more reference sensors attached to the patient's body in cases where the patient is likely to move to a material extent during the procedure, with the sensors being location sensors and used for identifying the patient motion so that it may be accounted and compensated for; one or more out-of-body transmitters, receivers, antennae, detectors, field generators, processors, or any combination thereof, interacting with these location sensor(s) to derive location information; and a computerized display comprising a depiction or an image of the body organ in which the procedure is performed and on which the location of the tool being navigated (or particularly of its distal tip) is superimposed and updated; or any combination thereof.

Apparatus comprising location sensors and/or image-guided navigation systems include, but are not limited to: Those comprising magnetic technologies (e.g., as described in the following US patents which are incorporated by herein reference: U.S. Pat. No. 5,558,091 to Acker et al., U.S. Pat. No. 6,233,476 to Strommer et al., U.S. Pat. No. 6,836,745 to Seiler et al., U.S. Pat. No. 5,744,953 to Hansen, U.S. Pat. No. 4,849,692 to Blood, U.S. Pat. No. 6,445,943 to Ferre et al., U.S. Pat. No. 6,784,660 to Ashe, U.S. Pat. No. 6,990,427 to Kirsch et al., U.S. Pat. No. 6,783,536 to Vilsmeier et al., U.S. Pat. No. 6,690,963 to Ben-Haim et al., or as developed by MediGuide Ltd. of Haifa, Israel, or by Biosense Webster Inc. of Diamond Bar, Calif., USA, or by Northern Digital inc. of Waterloo, Canada, or by BrainLAB AG of Kirchheim/Heimstetten, Germany, or by Ascension Technology Corporation of Burlington, Vt., USA). They additionally include location sensors comprising electromagnetic technologies (e.g., as described in the following US patents and patent applications which are incorporated herein by reference: U.S. Pat. No. 6,593,884 to Gilboa et al., U.S. Pat. No. 6,947,788 to Gilboa et al., U.S. Pat. No. 4,017,858 to Kuypers, U.S. Pat. No. 6,445,943 to Ferre et al., U.S. Pat. No. 6,636,757 to Jascob et al., US Patent Application 20060173291 to Glossop, or as developed by superDimension Ltd. (Herzliya, Israel), or by Polhemus Navigation Sciences, Inc. (Burlington, Vt., USA), or by Surgical Navigation Technologies, Inc. (Louisville, Colo., USA), or by Medtronic Navigation (Louisville, Colo., USA), or by Traxtal Technologies (Toronto, Canada)). They further include location sensors comprising electrical-impedance based technologies (e.g., as described by U.S. Pat. No. 5,553,611 to Budd et al., incorporated by reference herein). They additionally include location sensors comprising optical technologies, and those comprising voltage-sensing technologies (e.g., as described by U.S. Pat. No. 5,697,377 to Wittkampf, incorporated by reference herein). They further include location sensors comprising radiation-sensing technologies, wherein one or more very-low-dose irradiating elements is sensed and localized (e.g., triangulated) by out-of-body detectors (e.g., as described by US Patent Application 2007/0205373 to Komblau et al., or by US Patent Application 2007/0055090 to Neustadter et al., both of which applications are incorporated by reference herein, or as developed by NavoTek, Ltd., also known as VasTrack, Ltd., (Yokne'am, Israel)). They additionally include location sensors comprising ultrasonic or acoustic technologies (e.g., as described by U.S. Pat. No. 6,490,474 to Willis et al., or by U.S. Pat. No. 6,445,943 to Ferre et al., both of which patents are incorporated by reference herein). They further include location sensors comprising electrical-potential based technologies, or any combination of location sensors described herein.

The terms 'registration' and 'co-registration,' when used in the context of registering an image to a body organ (or to a portion thereof) such as the lungs of a patient, refer to the process of bringing the image and the organ (or portion thereof) into the same reference frame of coordinates. It is typically performed by correlating known marked features (also known as markers, or fiducials) observable in the image with the corresponding observable features in the actual body organ. The locations of the corresponding features in the actual organ are typically recorded by physically arriving at them with a tool equipped with one or more location sensors.

The terms 'registration' and 'co-registration,' when used in the context of registering two images (or sets of images) to one another, refer to the process of matching the images (or sets of images) to one another at one or more locations.

The terms 'maneuver' and 'maneuverability' (of a probe, a tool, a sheath, etc.) refer to the ability to deflect, tilt or steer the distal tip in one or more desired directions (such as the up/down and/or left/right directions). In the context of the present application and in the claims 'maneuverability' is defined as maneuverability that goes beyond pushing, pulling and/or rotating the distal section by applying a corresponding motion (i.e., push, pull or rotate) to the proximal section. In some embodiments, the mechanism supporting the maneuverability comprises steering wires such as those disclosed by U.S. Pat. No. 3,470,876 to Barchilon, which is incorporated by reference herein. In some embodiments, the mechanism supporting the maneuverability uses magnetic fields, such as with the Stereotaxis Magnetic Navigation System of Stereotaxis, Inc. (St. Louis, Mo., USA).

The term 'direct,' where used in the context of determining the location of a tool, means determining the location of the tool (or specifically of its distal tip) by means of location sensor(s) coupled to the tool.

The term 'indirect,' when used in the context of determining the location of a tool, means determining the location of the tool by determining the location of the sheath (or specifically of its distal tip) into which the tool is inserted and at the same time that the tool is inserted. The location of the sheath is determined by means of location sensor(s) coupled to the sheath. Typically, the location sensor(s) do not obstruct or block the tool from being inserted through the sheath's main channel at any phase of the sheath's insertion into the patient's body.

The term 'fluid' means gasses, liquids, and combinations of gasses and liquids. In the case of fluids flowing in the airways, those are mostly gasses; however they may also comprise liquids such as secretions and blood.

The term 'pre-procedure,' when used in reference to acquiring an image, describes acquisition of the image prior to the current medical procedure or prior to performance of the main portion of the medical procedure. For example, pre-procedure images may be acquired minutes, hours, or longer before a procedure is performed. For some applications, images are acquired while a patient is on a table in a treatment room, optionally anesthetized, optionally with medicals tools already in the patient's body, but before the main portion of the actual procedure in question is performed. In the context of the present patent application and in the claims, such images are also called "pre-procedure images."

B. Acquiring Images and Interpreting Images

Typically, images are acquired of the body organ (or portion of an organ) containing the luminal structure and to which the procedure is intended to be applied. In some embodiments, images are acquired prior to the procedure (i.e., "pre-procedure images"). Alternatively or additionally, images are acquired intermittently throughout the procedure. For some applications, the acquired images are observed and interpreted prior to the procedure that follows. In some embodiments, the observation and interpretation includes identifying desired locations for observation, diagnosis or treatment in the course of the procedure. Typically, the observation includes identifying paths leading to the locations. Further typically, the identification is performed manually by the operator of a computerized display on which the images are presented. In some embodiments, the identification is performed in a semi-automatic or automatic manner by software that runs on the computerized unit.

In the case of the lungs, the images typically comprise those produced by a pre-procedure CT chest scan. The images, once produced, are typically observed with viewing software (also known as a CT viewer) that typically provides an axial view, a sagittal view, a coronal view, and in most cases also a virtual endoscopy view. In some embodiments, intra-procedural endobronchial images (such as IVUS, or OCT, or MRI) are acquired. The use of such images in combination with the out-of-body (e.g., CT) images is described in further detail hereinbelow.

In the case of the coronary blood vessels, such images typically comprise those produced by CT, CT-angiography, Gamma Camera, ultrasound, MRI, OCT, or a combination thereof. Such modalities typically provide three-dimensional imaging data of the coronary tree.

In the case of the biliary tract, such images typically comprise those produced by CT, CT-angiography, ultrasound, 3D angiography performed by Endoscopic Retrograde Cholangiopancreatography (ERCP), or from any combination thereof.

C. Registering Acquired Images to the Patient's Body, and Co-Registering Images to One Another Embodiments of the current invention include the registration of an image to a tree-like luminal structure using a tree-to-tree registration method. FIGS. 1A and 1B are schematic illustrations of tree-like luminal structures typically identified by a human operator as being suitable for use with the tree-to-tree registration method, in accordance with respective embodiments of the present invention. Examples of such branches 30 are highlighted in the figures. FIG. 1A relates to the tracheobronchial tree, and FIG. 1B relates to the biliary tract. It should be noted that the branches used for registration do not need to intersect.

In other embodiments, a point-to-point registration technique is used, such as the one described by Solomon et al. in the article entitled "3D CT-Guided Bronchoscopy with Real-Time Electromagnetic Position Sensor," which is incorporated by reference herein.

Phases of the aforementioned tree-to-tree registration process typically comprise the following:
1. Constructing a virtual endoscopy image of the lumen or tree-like tract from three-dimensional imaging data. The data may be derived from any three-dimensional data (or multiple sets of two-dimensional data) generated by an imaging modality.
2. Presenting the virtual endoscopy data on a computerized display.
3. Traveling interactively within the virtual endoscopy while recording one or more Virtual Branch Lines in the tree-like tract. In some embodiments, the Virtual Branch Lines are recorded while traveling "forward" (e.g., from proximal to distal). Alternatively or additionally, the Virtual Branch Lines are recorded while traveling "backwards" (e.g., from distal to proximal). The Virtual Branch Lines typically stretch between one or more starting points and one or more ending points. An example of a starting point is the entry point to the tree or to a branch of the tree. An example of an ending point is the most distal point, along a branch of the tree-like luminal structure, which can be discerned in the pre-procedure images. In some embodiments, the user manually manipulates an input device (e.g., a joystick or a computer mouse) to travel along the center lines of two or more of the lumens in the tree-like luminal structure, and, by doing so, defines two or more Virtual Branch Lines. In some embodiments, a smoothing algorithm is applied to the two or more Virtual Branch Lines by suitable software. For some applications, the user aims to travel along portions of the walls (instead of along the center lines) of the luminal structure in two or more branches to produce two or more Virtual Branch Lines. In some embodiments, the user manually travels along the luminal structure while the software automatically computes and records a center line (or a wall line) along the travel for two or more branches of the luminal structure to produce, two corresponding Virtual Branch Lines. Alternatively or additionally, the user defines starting and ending points, and also one or more intermediate points, and the software travels in a virtual endoscopy mode along these points and defines two or more Virtual Branch Lines. For some applications, the Virtual Branch Lines are not only recorded but also marked interactively on the display. In some embodiments, the software can automatically repeat virtual travel along the Virtual Branch Lines, in any direction and as many times as are requested, once those Virtual Branch Lines were recorded. In some embodiments, the length of each Virtual Branch Line is computed and optionally is also displayed.
4. Physically entering the luminal structure with an endoscope, wherein a probe comprising one or more location sensors (typically at or towards its distal tip) is inserted through the endoscope's channel and typically protrudes from the endoscope's distal tip. Alternatively, the probe comprising the location sensor(s) is inserted into the luminal structure, not through an endoscope. In some embodiments, the probe comprises multiple location sensors along it. In some embodiments, the probe comprising the location sensor(s) is inserted into the luminal structure under some non-endoscopic form of intra-operative imaging. In some embodiments, the probe comprising the location sensor(s) is inserted through a sheath which also comprises one or more location sensors at or towards its distal section. In some embodiments, the probe comprising the location sensor(s) is inserted on its own, without a sheath. In some embodiments, the probe comprising the location sensor(s) is maneuverable. Typically, the probe comprising the location sensor(s) is a maneuverable sheath, such as the maneuverable sheath disclosed hereinbelow. For example, the probe comprising the location sensor(s) may be maneuverable by a robot, and/or the probe may be maneuverable from a remote location via tele-operation. Alternatively or additionally, the probe comprising the location sensor(s) is maneuverable by the application of magnetic fields. In some embodiments, the probe comprises an imaging capability in addition to the location sensor(s). In some embodiments, images produced by the imaging capability are co-registered and co-used together with images that were previously used for creating the virtual endoscopy. In some embodiments, the location sensor(s) is coupled directly to the endoscope itself so that the endoscope and the probe are one body.

5. Repeating with the aforementioned probe, in the course of its aforementioned progress and to the best of the operator's ability, Actual Branch Lines that are identical or similar to the Virtual Branch Lines created beforehand in the virtual endoscopy, and recording the lines. In some embodiments, the lines are recorded while pushing the probe forward (e.g., from proximal to distal). In some embodiments, the lines are recorded while pulling the probe backwards (e.g., from distal to proximal). The naturally elongated and narrow geometry of many body luminal structures typically facilitates the task. The location of the probe (typically the location of its distal tip) during the making of the Actual Branch Lines is recorded. The location of the probe is typically recorded by a location sensor which is coupled to the probe. In some embodiments, an imaging device acquires image frames of the probe within the subject's body, during the making of the Actual Branch lines. The location of the probe is determined during the making of the Actual Branch Lines by processing the image frames of the probe within the subject's body. In some embodiments, the recording of the location of the probe is gated to one or more cyclical physiological signals or processes in the patient's body including, but not limited to, ECG, blood pressure (e.g., systolic and diastolic), EEG, respiration, or any combination thereof. In some embodiments, the location sensor records respective locations of the probe at a same selected phase of the physiological cyclical process or signal. In some embodiments, the pre-procedure image is acquired at a given phase, and the recordings of the respective locations of the probe are gated to the same given phase. In some embodiments, the pre-procedure image is generated using image frames over multiple cycles, the acquisition of the image frames being gated to a given phase, and the recordings of the respective locations of the probe are gated to the same given phase. In some embodiments, algorithms that filter out or neutralize the effect of undesirable probe motion are applied when recording the Actual Branch Lines. For example, noise reduction algorithms and/or smoothing algorithms may be applied.

6. Overlaying the Virtual Branch Lines created in Step 3 with the Actual Branch Lines created in Step 5. In some embodiments, the overlaying is performed interactively by the user on a display. Alternatively or additionally, the overlaying is computed and performed by software running on a processor. In some embodiments, the overlaying is performed according to a best-fit algorithm. For some applications, the overlaying is performed while giving different relative weights to different parts of the Branch Lines, such as by giving more weight to the more distal portions than to the more proximal portions, and/or by giving more weight to the distal and proximal portions than to the middle portions, and/or by giving more weight to the starting and ending points (and optionally one or more easily-recognized points therebetween) than to the Branch Lines in between the points. In some embodiments, the overlaying is performed while giving different relative weights to different Branch Lines, such as while giving more weight to branches in a region or in an organ which is of clinical interest. Initial image-to-body registration is achieved at the end of Step 6. In some embodiments, certain of the above phases are repeated once or more in the course of the medical procedure, in order to retain or improve the accuracy of registration.

In some embodiments, the aforementioned tree-to-tree registration is performed in combination with point-by-point registration of some fiducials. In some embodiments, the discrete fiducials are artificial ones, in which case the point-by-point portion of the registration is typically performed according to the general principles taught by Solomon et al., in the article entitled "Real-time Bronchoscope Tip Localization Enables Three-dimensional CT Image Guidance for Transbronchial Needle Aspiration in Swine," which is incorporated herein by reference. In some embodiments, the discrete fiducials are natural ones, in which case the point-by-point portion of the registration is typically performed on anatomical landmarks according to the general principles taught by Solomon et al. in the article entitled "3D CT-Guided Bronchoscopy with Real-Time Electromagnetic Position Sensor," which is incorporated herein by reference).

The inventor hypothesizes that the tree-to-tree image-to-body registration method typically produces higher accuracy than conventional point-to-point registration methods, as it is less susceptible to an error in marking one or more specific points distorting significantly the outcome of the entire registration. For example, in the case of the bronchial tree, an error in marking any single fiducial point in the course of point-to-point registration as described by Solomon et al. and/or as presented by the superDimension/Bronchus system, and especially given that all such points are situated in the central areas of the lungs, may result in a more significant registration error with respect to target locations in the more peripheral areas of the lungs. In particular, a positional error in marking one or more central fiducial points may lead to a substantial angular error in the registration of the lungs as a whole and thus to a more substantial positional error when navigating to a target lesion situated in the periphery of the lungs (which is where most lesions are situated).

Furthermore, the inventor hypothesizes that the tree-to-tree image-to-body registration method also produces higher accuracy than the registration of a single path within the tree-like luminal structure. As noted previously, the tree-to-tree registration method calls for using two or more Branch Lines. Typically, the more the Branch Lines are spread apart and/or the larger the number of the Branch Lines is, the less susceptible would the outcome be to the negative effect of an error in marking any segment of a single line. For example in the bronchial tree, using Branch Lines from both the left and right lungs is typically useful for achieving higher accuracy in registration, and the same typically applies to using Branch Lines from both the upper and the lower lobes. Otherwise, registration may be distorted in a manner that could compromise its overall accuracy.

Typically, Branch Lines need not correspond to any specific path that a tool is anticipated to follow, or actually follows, during the procedure (following the tree-to-tree image-to-body registration). Rather, the primary consideration for their layout is typically to cumulatively achieve the best technically-possible coverage of the applicable luminal structure as a whole.

It should also be noted that tree-to-tree registration of an image to a luminal structure, as provided by embodiments of the current invention, is typically effective for a major portion of the luminal structure (or even to its entirety), including those parts of it that are situated beyond the Branch Lines. For example, in a coronary artery, the Branch Lines may be ones that are proximal to an occlusion (also known as an "obstruction") while the resulting registration may be effective for the continuation of that coronary artery at the distal side of the occlusion. Similarly, in the lungs, the Branch Lines may all be in major airways, which are typically disposed centrally, while the resulting registration may be effective for the entire respiratory tract, including peripheral regions of the airways of the lungs. It should also be noted that Lines used for registration need not necessarily be lines that are of clinical significance.

Some of the aforementioned embodiments of the tree-to-tree registration method are demonstrated in the following example for registering an image to the bronchial tree. The registration may, for example, be performed as a first step in the image-guided navigation of a tool to a target location that is beyond the reach (and vision) of the bronchoscope, such as a peripheral lesion that needs to be biopsied or ablated, or a lymph node that needs to be aspirated.

1. Generating a virtual bronchoscopy image of the respiratory tract from pre-procedure CT images, using imaging device 31 (e.g., as shown in FIGS. 1A and 1B).
2. Presenting the virtual bronchoscopy data on a computerized display 32 (e.g., as shown in FIGS. 1A and 1B).
3. Traveling interactively within the virtual bronchoscopy while recording two or more Virtual Branch Lines along the center lines of branches in the bronchial tree. The Virtual Branch Lines are typically recorded via an input unit in or coupled to a control unit such as a processor 34. Typically, in the bronchial tree, center lines are selected as the Virtual Branch Lines as they are the least affected by the natural expansion and contraction of the bronchial airways in the course of the respiratory cycle. Typically, the Virtual Branch Lines being traveled and recorded comprise several of the following, as can also be observed in FIG. 1A: from the trachea to the Left Upper Lobe (LUL) main bifurcation (or "junction") and potentially further into the LUL; from the trachea to the Left Lower Lobe (LLL) junction and potentially further into the LLL; from the trachea to the Right Upper Lobe (RUL) junction and potentially further into the RUL; from the trachea to the Right Middle Lobe (RML) junction and potentially further into the RML; from the trachea to the Right Lower Lobe (RLL) junction and potentially further into the RLL; and from the trachea to any other junction that is visible in the virtual endoscopy. Typically, the more Virtual Branch Lines are recorded and the more spread apart those lines are, the more accurate the registration will eventually be. Using Branch Lines from both the left and right lungs is typically useful for achieving high accuracy in registration, and the same typically applies to using Branch Lines from both the upper and the lower/middle lobes. The scope of the present invention includes using non-intersecting branches of tree-like luminal structure for performing tree-to-tree registration using the techniques described herein.
4. Entering the bronchial airways with a bronchoscope, while a probe comprising one or more location sensors is inserted through the bronchoscope's channel. The location sensors are typically situated at or towards the distal tip of the probe. In some embodiments, the probe is a maneuverable and localizable sheath as described hereinbelow. In some embodiments, a tool is already inserted through the maneuverable and localizable sheath. For as far as the bronchoscope can physically proceed within the airways, the probe is inserted together with the bronchoscope, typically slightly protruding out of the bronchoscope's distal tip. Once the bronchoscope has reached a point in its travel where it is too large in its diameter to proceed further, and should the Virtual Branch Lines marked beforehand in the virtual bronchoscopy continue ahead of that point, the probe may be pushed ahead without the bronchoscope (typically, while the operator is using a technique such as intra-operative fluoroscopy to avoid approaching the pleura and risk causing a pneumothorax).
5. Traversing with the aforementioned probe, in the course of the aforementioned progress of the (bronchoscope and the) probe and to the best of the operator's ability, two or more Actual Branch Lines that are identical or similar to the corresponding Virtual Branch Lines created beforehand in the virtual endoscopy. Typically, in order to avoid irritation of the patient by touching the bronchial walls (and unless the patient is anesthetized or very heavily sedated), the Actual Branch Lines are typically designated to be center lines. In some embodiments, gating to respiration is applied when recording the locations of the probe along the Actual Branch Lines, such that movement of the bronchial tree in the course of the respiratory cycle is accounted for. In some embodiments, respective locations of the probe are recorded at the same selected phase in the patient's respiratory cycle, the phase typically being identified by a respiration sensor, a displacement sensor, and/or a vibration sensor. In some embodiments, the recordings of the respective locations of the probe are gated to a phase during which the pre-procedure CT image was acquired.
6. Overlaying the Virtual Branch Lines created in Step 3 with the Actual Branch Lines created in Step 5. The overlaying is typically performed by processor 34 (e.g., as shown in FIGS. 1A and 1B). In some embodiments, greater weight is given to the well-defined bifurcation points at the ends of, or along, the Branch Lines than to the segments of the Branch Lines in between the points. Alternatively or additionally, greater weight is given to the Branch Lines in the more distal and narrower airways (where the center line is easier to identify and travel along with greater accuracy) than those along the more proximal and wider airways.

In some embodiments, and for example in the respiratory tract, the aforementioned probe comprising one or more location sensors and applied for CT-to-body registration also comprises, or is coupled to, an endoluminal imaging probe (in the case of the lungs, an endobronchial probe), such as EBUS, OCT or MRI, such that the position of the endoluminal imaging source relative to the location sensor(s) is known. In some embodiments, the probe comprising one or more location sensors is a sheath, and the endoluminal imaging probe is inserted through a channel of that sheath such that the position of the endobronchial imaging source relative to the location sensor(s) is known. In some embodiments, when recording the Actual Tree Branches, the intra-operative images generated by the endoluminal imaging probe inserted within the sheath are therefore coupled with location coordinates generated by the location sensor(s) in the sheath at each location along the Actual Tree Branches. Later on in the registration process, when the Actual Tree Branches are co-registered with the Virtual Tree Branches to achieve registration of the pre-procedure images to the patient's body as currently situated on the procedure bed, the location coordinates of the aforementioned intra-operative endoluminal images go through a similar transformation such that individual intra-operative endoluminal images remain matched with a specific location along a Branch. Consequently, once registration of the aforementioned pre-procedure CT images to the patient's lungs is achieved, images produced by the endoluminal imaging probe are also co-registered with the CT images such that locations on the CT images are matched together with corresponding endoluminal images. In some embodiments, the endoluminal images are stored, and retrieved at a later time by pointing at the corresponding location on the CT images.

It should be noted that the co-registration among the CT images and the endobronchial images is achieved regardless of whether the CT-to-body registration was performed point to point, tree-to-tree, or any combination thereof.

Separately, some of the aforementioned embodiments of the tree-to-tree registration method are demonstrated in the following example for registering an image to the biliary tract and the duodenum. The registration may, for example, be performed as a first step in an image-guided insertion of an endoscopic tool to retrieve a stone that is situated beyond the reach (and vision) of the duodenoscope, such as in the bile duct.

1. Generating a virtual endoscopy image of the biliary tract (e.g., the duodenum, the bile duct, the pancreatic duct, the gallbladder) from CT images, or from ultrasound images, or from 3D angiography performed in an Endoscopic Retrograde Cholangiopancreatography (ERCP), or from any combination thereof. The images are acquired with an imaging device 31, the device being as shown in FIG. 1B.
2. Presenting the virtual endoscopy data on a computerized display 32, as shown in FIG. 1B.
3. Traveling interactively within the virtual endoscopy while recording two or more Virtual Branch Lines. For example, one Virtual Branch Line may be recorded along the center line (or the walls) of a portion of the duodenum until the Papilla of Vater, with two additional Virtual Branch Lines (as can also be observed in FIG. 1B) then recorded within the ducts (i.e., from the Papilla of Vater and onwards into the ducts).
4. Entering the duodenum with a duodenoscope, while a probe comprising one or more location sensors (typically situated at or towards its distal tip) is inserted through the duodenoscope's working channel. Until the Papilla of Vater, the probe is inserted together with the duodenoscope, typically protruding slightly out of the duodenoscope's distal tip. Once the lumen is too narrow in its diameter in order to allow the duodenoscope to proceed further, which is typically from the Papilla of Vater and onwards, the probe is pushed ahead without the duodenoscope (but potentially under the guidance of some other form of imaging such as angiography or fluoroscopy) through the ducts. In the aforementioned embodiment wherein the probe comprises an imaging probe, the images acquired by that probe may be co-registered with the angiographic or fluoroscopic image. In some embodiments, the co-registration is achieved by means of identifying a location of the imaging probe within the angiographic or fluoroscopic image while the probe is acquiring the images.
5. Guiding the aforementioned probe, in the course of its aforementioned progress and to the best of the operator's ability, along two or more Actual Branch Lines that are identical or similar to those created beforehand in the virtual endoscopy. (Due to the relatively small diameter of the ducts, the Actual Branch Lines typically tend to be center lines in the ducts.)
6. Overlaying the Virtual Branch Lines created in Step 3 with the Actual Branch Lines created in Step 5, the overlaying typically being performed by processor 34, the processor as shown in FIG. 1B.

Separately, some of the aforementioned embodiments of the tree-to-tree registration method are demonstrated in the following example for registering an image to coronary blood vessels. The registration may, for example, be performed as a first step in an image-guided placement of the left-side leads of an implantable cardiac rhythm management device in a coronary sinus branch.

1. Generating a virtual endoscopy image of the coronary sinus from MRI images, or from ultrasound images, or from 3D angiography, or from CT angiography, or from a combination thereof.
2. Presenting the virtual endoscopy data on a computerized display.
3. Traveling interactively within the virtual endoscopy while recording two or more Virtual Branch Lines along the center line of the coronary sinus and of its branches such as the branch leading to the designated location(s) for placing the lead(s).
4. Entering the coronary sinus with a sheath or a steerable sheath, and wherein a probe comprising one or more location sensors (typically positioned at or towards its distal tip) is inserted through the sheath so that the location sensor is aligned with the distal tip of the sheath. In some embodiments, the probe comprising the one or more location sensors is a lead placement probe. In some embodiments, the probe comprising the one or more locations sensors is the lead itself. In some embodiments, the steerable sheath is constructed according to the principles described by U.S. Pat. No. 3,470,876 to Barchilon, which is incorporated herein by reference. In some embodiments, insertion of the sheath or steerable sheath is performed under some form of intra-operative imaging including, but not limited to, fluoroscopy, angiography, CT, or any combination thereof.
5. Guiding the aforementioned sheath and probe, along the coronary sinus and to the best of the operator's ability, along two or more Actual Branch Lines that are identical or similar to the Virtual Branch Lines created beforehand in the virtual endoscopy. (Due to the relatively small diameter of the coronary sinus and its branches, the Branch Lines will typically tend to be center lines.)
6. Overlaying the Virtual Branch Lines created in Step 3 with the Actual Branch Lines created in Step 5.

D. Inserting Tools, such as Via a Maneuverable and Localizable Sheath, Navigating the Tools within the Luminal Structure and Utilizing them at Desired Locations In some embodiments, subsequent to the aforementioned registration of images to the luminal structure, tools are inserted into the luminal structure and navigated to their targets while using an image-guided navigation system. The current locations of the tools, superimposed on the aforementioned registered images that now serve as a roadmap, are typically presented on a computerized display.

In some embodiments, in the case of performing the procedure via the bronchial tree, the roadmap typically comprises the aforementioned pre-procedure CT images that were registered to the patient's body, such as via the aforementioned tree-to-tree and/or point-to-point methods.

In some embodiments, wherein images generated by an endobronchial probe were already co-registered with the CT images at the time CT-to-body registration was performed, the endobronchial images are already associated with locations on the aforementioned CT roadmap. The images generated by an endobronchial probe may comprise EBUS, OCT, MRI, or any combination thereof.

In some embodiments, in the case of performing the procedure via the bronchial tree, the computerized display comprises one or more of the following views at the current location of the tool: sagiffal CT images, coronary CT images, axial CT images, virtual endoscopy images, a stack of axial CT images from the distal tip of the tool and forwards, a three-dimensional reconstruction from CT of both lungs or only of the lung in which the procedure is due to take place, the aforementioned images generated by an endobronchial probe presented in two-dimensional slices, and a three-dimensional reconstruction of the aforementioned images generated by an endobronchial probe.

The views are typically updated to reflect the current location of the tool, as the location is updated in the course of navigating the tool. In some embodiments, the current location of the tool is displayed relative to the target location at which the tool is desired to arrive.

In some embodiments, tools are inserted through a maneuverable and localizable sheath. Embodiments of the sheath are disclosed below. The maneuverable and localizable sheath typically provides standard, off-the-shelf tools with added maneuverability and localizability which they typically lack. The maneuverability and localizability are typically useful for navigating these tools to their target locations through the luminal structure when the target locations are outside the reach and vision of an endoscope through which the tools may be inserted.

In some embodiments, the maneuverable and localizable sheath is inserted at first with its main channel being empty, while a tool is inserted through that sheath only in a later phase. In some embodiments, the maneuverable and localizable sheath is inserted together with a tool inserted through its main channel, with the tool typically acting as a center support that may provide the sheath with improved pushability and/or maneuverability.

FIG. 2 is a schematic illustration of a maneuverable and localizable sheath 1, with a tool 4 inserted through the sheath. In some embodiments, maneuverable and localizable sheath 1 is inserted into the body through a channel 2 of an endoscope 3. Tool 4 is inserted through a main inner channel 5 of sheath 1. Typically, the distal tip of the endoscope is maneuverable such that it can be tilted in two (e.g., up/down), or sometimes four (e.g., up/down and left/right), directions. Typically, tool 4 lacks any built-in maneuverability.

In the context of the bronchial tree, the endoscope being used is typically a bronchoscope. The bronchoscope is typically flexible, though in some cases it may also be rigid. In another embodiment, a flexible bronchoscope is inserted through a rigid bronchoscope.

Typically, sheath 1 provides tool 4 with maneuverability when tool 4 is pushed through and further ahead of endoscope 3, such that the maneuverability provided to tool 4 by endoscope 3, by means of the endoscope's own maneuverable tip, is no longer applicable or sufficient. The target location at which tool 4 is due to arrive is, in such cases, typically outside the reach of endoscope 3 due to reasons such as endoscope 3 being too short to reach the target location, or the diameter of endoscope 3 being too large compared with the diameter of a body lumen leading to the target location, or the maneuverability of endoscope 3 being insufficient to negotiate all of the turns in the path leading to the target location, etc.

Specifically with respect to the bronchial tree, the maneuverability of the aforementioned sheath is typically useful in the situations such as the following:

Where the path leading to a target location comprises turns that the bronchoscope cannot fully negotiate;

Where an airway leading to a target location is obstructed and thus too narrow for the bronchoscope to traverse;

Where a target location is situated outside the bronchi in the surrounding tissue, which is often the case with suspected lung masses;

Where the target location is a lymph node adjacent to the bronchi, and wherein the specific procedure may be Trans Bronchial Needle Aspiration (TBNA) of the lymph node;

Where the target location is situated in the peripheral areas of the lung where the bronchial airways are typically narrower than the shaft of the bronchoscope. In this case, the bronchoscope is typically insertable until the third- or fourth-level junction (out of typically twenty or more) in the bronchial tree, while the tool is pushed ahead farther, and negotiates further turns without the bronchoscope, until it can reach the target in the periphery.

Other examples, outside the bronchial tree, where maneuverability of the sheath is useful for negotiating luminal structures include the following:

In the biliary tract where the target location is within one of the narrow ducts beyond the Papilla of Vater such that the diameter of the endoscope is too large to reach it. In such cases, the endoscope typically reaches only until the Papilla of Vater, while the endoscopic tool is pushed ahead further through the Papilla and into the ducts without the endoscope. However the tool still negotiates the junction leading to the desired specific duct.

In the nasal sinuses where the passages leading to the target are very narrow and/or obstructed compared with the endoscope's diameter.

Thus, in accordance with some embodiments, sheath 1, with tool 4, is often pushed considerably beyond and ahead of the distal tip of endoscope 3. In such embodiments, tool 4 which typically lacks built-in maneuverability can no longer rely on the maneuverability of endoscope 3, and instead relies on the maneuverability of sheath 1.

In another embodiment, maneuverable sheath 1 is inserted into the body not via an endoscope. Examples of medical procedures for which it may be useful to operate the maneuverable sheath 1 without an endoscope include using the sheath for the placement of the leads of electrophysiological devices in the heart or in the coronary blood vessels. One such procedure is known specifically as Left Side Lead Placement, in which a lead is inserted from within the heart through the coronary sinus and placed on the outside of the left side of the heart. A second example for the type of procedures where the sheath would typically be used without an endoscope is for the insertion of a wire or probe that penetrates through a partial of total occlusion in coronary or peripheral arteries. A third example of a procedure in which the sheath would typically be used without an endoscope is for constructing a bypass around a total occlusion in a coronary artery.

FIGS. 3A-C are schematic illustrations of respective views of a shaft of a maneuverable, and typically localizable, sheath, in accordance with an embodiment of the present invention. FIG. 3A is a view from the distal side, FIG. 3B is a view from the proximal side, and FIG. 3C is a longitudinal cross section.

In some embodiments, sheath 1 comprises a sheath body 7 which defines a main inner channel 5. In the context of the present patent application and in the claims, the sheath body is defined as the portion of the sheath which is between the outer circumference of main channel 5 and the outer circumference of the sheath. In some embodiments, sheath body 7 defines an additional channel 6. It is noted that in the context of the present patent application and in the claims, anything disposed within additional channel 6 is defined as being disposed within sheath body 7. It is further noted, that in the context of this application and in the claims, anything that is disposed within main channel 5 is not defined as being disposed within sheath body 7.

In some embodiments, main channel 5 is used for tool insertion. In some embodiments, channel 6 is used for insertion and placement of one or more location sensor(s) 18. In some embodiments, by being placed within channel 6, the location sensors become effectively embedded in the body of the sheath. In some embodiments, the location sensor(s) are actually embedded in a solid portion of sheath body 7. In some embodiments, channel 6 does not exist, in which case main channel 5 may be generally concentric with the shaft of sheath 1. In some embodiments, sheath 1 comprises additional channels for the insertions of tools and/or location sensors. In some embodiments, sheath 1 comprises additional channels for tool insertion.

In some embodiments, the outer surface of sheath body 7 is coated with a smooth material such as silicone or Teflon to facilitate the insertion of sheath 1 through an endoscope. In some embodiments, sheath body 7 of sheath 1 comprises a braid of wires in order to make it further resistant to kinks and punctures. In some embodiments, sheath body 7 comprises see-through section(s) so that the progress of tools through its channel(s) can be observed more easily, such as by an endoscope.

In some embodiments, a ring 8 is attached to the distal tip of sheath 1. In some embodiments, ring 8 is radiopaque, so that it can be easily seen in fluoroscopy. In some embodiments, radiopaque marker(s) are situated at or towards the distal tip of sheath 1.

Typically, steering wires 10 and 11 join sheath 1 at its proximal end and connect to distal ring 8. Steering wires 10 and 11 control tilting of the distal section of sheath 1 in the up and down directions. In some embodiments, steering wires 10 and 11 are attached longitudinally to the wall of main channel 5. In some embodiments, steering wires 10 and 11 are inserted along channels 12 and 13, the channels being defined by sheath body 7 of sheath 1.

Further typically, steering wires 14 and 15 join sheath 1 at its proximal end and connect to distal ring 8. Steering wires 14 and 15 control tilting of the distal section of sheath 1 in the left and right directions. In some embodiments, steering wires 14 and 15 are attached longitudinally to the wall of main channel 5. In some embodiments, steering wires 14 and 15 are inserted along channels 16 and 17, the channels being defined by sheath body 7 of sheath 1.

In some embodiments, only one pair of steering wires exists, controlling tilting in only two directions (e.g., up/down or left/right).

All steering wires are typically connected at their proximal ends to a steering actuator which causes the tilting of the distal tip of sheath 1 by pulling one or more wires while not pulling, or releasing the tension on, one or more other wires. For example, pulling wire 10 (while not pulling, or releasing the tension on, wire 11) causes the distal tip of sheath 1 to tilt in the up direction. Also, for example, pulling wires 10 and 14 at the same time (while not pulling, or releasing the tension on, wires 11 and 15) causes the distal tip of sheath 1 to tilt in an intermediate direction between up and left.

Sheath 1 typically comprises one or more location sensor(s) 18, the sensor(s) typically being situated at or towards the distal tip of the sheath. In some embodiments, multiple location sensor(s) 18 are situated at several positions along the length of sheath 1. In some embodiments, location sensor(s) 18 are situated within channel 6. In some embodiments, location sensor(s) 18 are wired, and the wire(s) 19 leading to them are positioned within channel 6 as well.

In some embodiments, location sensor(s) 18, as well as wire(s) 19 if applicable, are embedded within a solid portion of sheath body 7 of sheath 1. Alternatively or additionally, location sensor(s) 18, as well as wire(s) 19 if applicable, are positioned within a groove in the outer surface of the sheath body of sheath 1. In accordance with such embodiments, the sheath may define a single channel 5.

In some embodiments, location sensor(s) 18 are removable. In another embodiment, location sensor(s) 18 are both removable and reusable. Such reusability typically lowers the cost per each use. If location sensor(s) 18 are removable and wired, then the wire(s) 19 leading to them are typically also removable.

FIGS. 4-6 are schematic illustrations of respective embodiments of steering actuators and handles for maneuverable sheaths. In some embodiments, as illustrated in FIG. 4, steering actuator 20 comprises two knobs 21 and 22, one to which wires 10 and 11 of FIGS. 3B and 3C are connected and which controls the up-down tilt by its rotation, and the second to which wires 14 and 15 of FIGS. 3B and 3C are connected and which controls the left-right tilt by its rotation. Typically, the knobs are situated either perpendicularly or in parallel to one another. Each knob may also be locked once a certain tilt is to be fixed, and subsequently unlocked when the tilt no longer is to be fixed.

In some embodiments, as illustrated in FIG. 5, actuator 20 comprises two levers 23 and 24, one to which wires 10 and 11 of FIGS. 3B and 3C are connected and which controls the up-down tilt by its pulling, and the second to which wires 14 and 15 of FIGS. 3B and 3C are connected and which controls the left-right tilt by its pulling. Typically, the levers are situated either perpendicularly or in parallel to one another. Each lever may also be locked once a certain tilt is to be fixed, and subsequently unlocked when the tilt no longer is to be fixed.

In some embodiments, as illustrated in FIG. 6, actuator 20 comprises a joystick 25 to which all steering wires are connected and which controls tilting in any of the available directions by its manipulation in a direction corresponding to the desired direction of tilting. The joystick may also be locked once a certain tilt is to be fixed, and subsequently unlocked when the tilt no longer is to be fixed.

The ability to lock the tilt of sheath 1 is typically useful in a number of cases. One such case is where the physician or nurse operating sheath 1 tires of holding actuator 20 and yet wishes to keep tool 4 in place and/or in the desired tilting angle. A second such case is where the operator of sheath 1 no longer has a hand available for operating actuator 20 and yet wishes to keep tool 4 in place and/or in the desired tilting angle. A third such case is where tool 4 needs to be retrieved and reinserted multiple times in the course of the procedure (such as when taking and depositing multiple biopsies, for example), in which case sheath 1 remains in place (and/or in the desired tilting angle) which facilitates the repeat insertion of tool 4 to its target location. A fourth such case is when, in the course of the same medical procedure, multiple different tools need to be inserted one after the other through sheath 1 to the same target location or to nearby target locations.

In the case of the bronchial tree, locking the tilt of the sheath may be of particular importance where the sheath is within an airway, but the target location for the utilization of the tool inserted through the sheath is within the tissue surrounding the airway. In fact, a considerable proportion of suspected lung masses are positioned not within an airway but rather in a tissue next to the airway. In such a case, preserving the desired tilt typically helps in increasing the probability of the tool indeed reaching its desired location. The same applies where the procedure being performed is Trans Bronchial Needle Aspiration and the target location is a lymph node which is situated outside the airway.

In some embodiments, such as upon arriving at a desired location, the distal tip of sheath 1 is further securable to the tissue adjacent to it so that its location is generally fixed, by means of one or more inflatable (and subsequently deflatable) balloons that are inserted though one or more of channels 5 and 6. In some embodiments, the balloons are inflatable with air and/or saline. In some embodiments, the balloons are coupled to sheath body 7.

Steering actuator 20 is typically part of handle 26. Handle 26 is typically coupled (such as by a fastener or a clamp) to the proximal port of channel 2 of endoscope 3 (of FIG. 2) or to the gripping handle of endoscope 3. The coupling of handle 26 to endoscope 3 is typically reversible. In some embodiments, the detachable coupling is implemented using a clip.

In some embodiments, handle 26 is detachable from the shaft of sheath 1. In such a case steering wires 10, 11, 14 and 15 of FIGS. 3B and 3C are plugged into handle 26 by means of a detachable connection. The detachable connection of steering wires 10, 11, 14 and 15 of FIGS. 3B and 3C to handle 26 comprises connecting elements of any detachable type such as screws, nuts, bolts, clips, pips, magnets, plugs, hooks, threads, clasps, clamps, or any combination thereof. Compared with a non-detachable handle, a detachable handle lends itself more easily to reusability and thus lowers the cost per each use.

In the course of a medical procedure wherein sheath 1 is inserted through an endoscope, the sheath is typically secured to the proximal port of channel 2 by a luer, fastener, adapter, or any combination thereof.

In some embodiments, sheath 1, comprising one or more location sensor(s) 18, is localizable but not maneuverable. In such cases, the sheath does not comprise steering wires 10, 11, 14 and 15, nor does it comprise steering actuator 20. In some embodiments, in such cases sheath 1 also does not comprise handle 26.

At the beginning of the medical procedure in which sheath 1 is inserted through an endoscope, the sheath is typically aligned inside endoscope 3 such that the steering directions (e.g., up, down, left, right) of the distal tip of sheath 1, as set by actuator 20, correspond to those of the distal tip of endoscope 3. The alignment is typically performed manually by the physician or nurse responsible for the endoscope.

As a result of the described alignment, the operation of sheath 1 is more intuitive to the operator of endoscope 3. For example, when navigating in the bronchial tree, it would typically be easier for the operator of the bronchoscope if sheath 1 is already aligned with the bronchoscope such that the up/down and left/right directions of the two are typically the same (precisely or closely). In such cases, negotiating bifurcations in the bronchial tree with the sheath, where the bifurcations are situated beyond the bronchoscope's own reach, would typically resemble, from the operator's point of view, negotiating the bifurcations as was done with the bronchoscope earlier in the procedure for bifurcations that were still within its reach.

In some embodiments, once the alignment is achieved it is then secured by the aforementioned luer, fastener, adapter, or a combination thereof.

In some embodiments, the distal tip of tool 4 remains located at the distal tip of sheath 1 or right ahead of it following its insertion into the sheath, and does not shift uncontrollably forwards or backwards relative to sheath 1. In some embodiments, that is achieved by securing tool 4 after its insertion to the proximal port of channel 2, or to the section of sheath 1 that extends proximally out of that port. The securing is typically achieved by a luer, fastener, adapter, or any combination thereof. In a second embodiment, that is achieved by putting a mark (such as with a color marker or crayon) that needs to be visually kept in its relative place. In a third embodiment, that is achieved by placing a clip on the section of tool 4 that extends proximally from the proximal segment of sheath 1 and verifying that the mark or clip remains in place during the use of tool 4.

With respect to any of the aforementioned figures, location sensor(s) 18 typically facilitates the use of the maneuverable sheath in conjunction with the navigation system, when (a) the target location at which sheath 1 and tool 4 are due to arrive is outside the range of the vision of an endoscope through which sheath 1 is inserted, (b) the endoscope's vision capability is dysfunctional or malfunctioning, or (c) an endoscope is not being used at all in conjunction with maneuverable sheath 1. For example, in the case of navigating through the bronchial tree, then (for any of the situations listed previously wherein the target location is outside the bronchoscope's own vision) the distal tip of the maneuverable and localizable sheath is superimposed on the pre-procedure CT images that were previously registered to the lungs and serve as a roadmap.

The location of tool 4 is typically deduced indirectly, i.e., it is deduced from the location of sheath 1 to which location sensor(s) 18 is coupled, while tool 4 is situated in sheath 1. The same applies to determining the location of additional tool(s) or probe(s) inserted through one or more of the available channels of sheath 1. In such cases, multiple tools inserted through sheath 1 are localized concurrently.

Typically, tools being inserted through the sheath protrude through its distal tip (e.g., by about 0.5 cm to 1.5 cm). Therefore in some embodiments, for calculating the location of the tool(s), a matching offset equal to the extent of protrusion of the tool(s) from the sheath is added to the location coordinates provided by the location sensor. In some embodiments, the tool protrudes from the distal tip of the sheath by a fixed amount. Alternatively, the tool protrudes from the distal tip of the sheath by a measurable variable amount. For example, the sheath may be of a known length and the tool may have markings at its proximal end indicating the length of a portion of the tool that has been inserted into the sheath. Based on the indication of the markings at the proximal end of the tool, as well as the known length of the sheath, the length of the distal portion of the tool that protrudes from the distal end of the sheath can be determined.

Embodiments of the current invention typically allow an off-the-shelf tool that can physically fit through a channel of the sheath to be localized and navigated, typically without any adaptations (such as incorporating a location sensor) made to the tool itself. In other words, it typically turns non-localizable tools into localizable tools, without needing to reconfigure the non-localizable tools.

Among the aforementioned magnetic and electromagnetic technologies listed under the definitions of a location sensor and a navigation system, of notable applicability are implementations where the location sensor(s) comprise only longitudinal coil(s). In such cases, the outer diameter of the location sensor is particularly small, when compared to magnetic or electromagnetic location sensors that comprise coils situated in multiple directions.

An example of a location sensor comprising only longitudinal coil(s) and offering a relatively small outer diameter is one with an outer diameter of approximately 0.25 mm. Such location sensors have been presented by MediGuide, Ltd. (Haifa, Israel) and by Ascension Technologies, Inc., (Burlington, Vt., USA) as described hereinabove in the Background.

Compared with location sensors comprising coils disposed in multiple directions, the location sensors comprising only longitudinal coil(s) typically do not provide any location information on the roll. However, they typically do provide location information in most or all of X, Y, Z, pitch and yaw.

For some embodiments of the current invention, the information on the roll is typically not necessary, and particularly so if the directionality of the sheath is already aligned with the directionality of the endoscope through which it is inserted as described previously. Therefore, according to some embodiments of the current invention, a location sensor (in cooperation with a sheath and other apparatus as described hereinabove) comprising only longitudinal coil(s), and having a small outer diameter is used despite the fact that the sensor cannot be used to detect information regarding the roll. The small outer diameter of the location sensor typically facilitates incorporation of the sensor within the sheath or insertion through a channel in the sheath without blocking or obstructing the insertion of a tool through the main channel of the sheath, as described hereinabove.

For example, when using location sensor(s) comprising only longitudinal coil(s), a maneuverable sheath can fit into the 2.8 mm channel of a common bronchoscope (for example, the outer diameter of the sheath may be 2.5 mm to 2.7 mm, while its main channel accommodates a 1.2 mm to 1.8 mm tool (which are typically standard diameters for off-the-shelf bronchoscopic tools) and a location sensor of up to 0.3 mm in diameter. In some embodiments, both tool and sensor(s) are inserted concurrently through the sheath's main channel. Alternatively or additionally, the location sensor(s) are inserted via the sheath's secondary channel. Further alternatively or additionally, the location sensor(s) are effectively embedded within the wall of the sheath as the wall is defined by the sheath's main channel. In such configurations, the location sensor and the tool typically do not block or obstruct one another at any time that the sheath is inserted into the patient's body and the tool is inserted through the main channel of the sheath.

Separately, among the aforementioned radiation-sensing technologies listed under the definitions of a location sensor and a navigation system, the location sensor may comprise one or more particles or specks of very-low-dose radiating elements overlaid on, or adhered to, or coating, or embedded within, sheath 1 (or particularly its distal tip). In such cases, a single inner channel may suffice for the tools inserted through the sheath to still be localizable.

It should be noted that, in any of the embodiments of the sheath disclosed herein and during any phase in the insertion of the sheath into the patient's body:

The location sensor(s) typically do not block or obstruct the main channel of the sheath.

The effective inner diameter (i.e., the diameter available for tool insertion) of the main channel of the sheath at a section of the sheath at which location sensor(s) are positioned is typically not substantially smaller than the inner diameter of neighboring sections of that channel.

The outer diameter of the sheath at a section of the sheath at which location sensor(s) are positioned is typically not substantially larger than the outer diameter of neighboring sections of the sheath.

The position of the location sensor(s) relative to the rest of the sheath typically does not change.

In embodiments in which the location sensor(s) are magnetic or electromagnetic coils, they typically do not loop around a channel used for tool insertion, rather the coils are disposed within the body of the sheath as described hereinabove. The use of magnetic or electromagnetic coils as the location sensor(s) typically does not place a large constraint on achieving the smallest possible outer diameter for the sheath, as the coils are typically less than 0.3 mm in diameter.

In some embodiments, once the maneuverable and localizable sheath is navigated to the target location such that its distal tip is at or near the target location, then one or more tools that are inserted through the sheath, in parallel or sequentially, are applied to the target location.

E. Co-Utilizing Intra-Operative Imaging

In some embodiments, when navigating within the luminal structure, a form of intra-operative imaging is co-utilized together with the aforementioned pre-procedure imaging. In some embodiments, the co-utilization is performed after the time the intra-operative images where generated. In some embodiments, the pre-procedure imaging is generated by an imaging source situated outside the body portion, such as a CT in the case of the lungs, while the intra-operative imaging is generated from within the body portion, such as via an endoluminal imaging probe.

Embodiments of such endoluminal imaging probes include, but are not limited to, an endoluminal ultrasound probe (such as the EBUS from Olympus America, Inc. in the case of the lungs, or the IVUS from Boston Scientific or Volcano in the case of the coronary blood vessels), an MRI probe (such as those developed by TopSpin Medical of Lod, Israel, including the IVMRJ), an optical fiber, an Optical Imaging probe, an infra-red imaging probe, and an Optical Coherence Tomography probe.

In some embodiments, images generated by the endoluminal probe are co-registered at the beginning of a procedure with images generated by an imaging source from outside the body portion. An example, in the case of the lungs, is the co-registration of intra-operative EBUS images with pre-procedure CT images, concurrently with the registration of those CT images to the patient's lungs, as described hereinabove in the Registration section of this application. As a result, in addition to the CT images serving as a roadmap for navigation, locations on that CT roadmap are matched together with individual endoluminal image frames from the EBUS.

In another embodiment, the image-to-body registration and the image-to-image co-registration are performed separately. In the example of the lungs, CT-to-body registration is performed at the beginning of the procedure to create a CT roadmap. (The registration may be tree-to-tree, or point-to-point, or any combination thereof.) Subsequently, the endoluminal imaging probe is inserted into a channel of the aforementioned maneuverable and localizable sheath, such that the position of the imaging source in the probe relative to the location sensor(s) in the sheath is known. For example, tool 4 of FIG. 2 may comprises an endoluminal imaging device. The imaging probe is navigated together with the sheath to a desired location. Images captured by the imaging probe along the path are coupled, by means of the location sensor(s) in the sheath, to location coordinates along the path. Those location coordinates are already identifiable on the CT roadmap. Consequently, those endoluminal images also become matched to corresponding locations on the CT roadmap.

In some embodiments, when subsequently navigating a tool inserted within (and together with) the aforementioned maneuverable and localizable sheath to a desired location, the computerized display comprises not only the superposition of the tool upon the pre-procedure images (such as CT in the example of the lungs) serving as a roadmap, but also the corresponding intra-operative endoluminal images as recorded in a preceding step at each same (or similar) set of location coordinates. In some embodiments, the corresponding intra-operative image is presented simultaneously, but on a separate display.

In some embodiments, the images previously acquired by the endoluminal probe are presented as a virtual endoscopy view through which the localizable sheath progresses. In some embodiments, the same applies to the pre-procedure images, such that the localizable sheath is displayed as progressing through the two forms of virtual endoscopy concurrently. In some embodiments, the localizable sheath is displayed as progressing through a virtual endoscopy image that is a combination (such as an overlay or a fusion) of the two virtual endoscopy views, i.e., the one from the pre-procedure imaging (such as CT) and the one from the intra-operative endoluminal imaging (such as the EBUS).

In some embodiments, presenting images from both sources with respect to a current location is of greater clinical value than that provided by each of the imaging sources separately. In some embodiments, a user receives a form of intra-operative, near-real-time imaging from the endoluminal images in addition to the typical pre-procedure imaging, which typically enhances the real-time nature of the image-guided procedure.

In some embodiments, the aforementioned intra-operative imaging is also utilized to make intra-procedural corrections to the prior registration of the pre-procedure images to the luminal structures. In some embodiments, the imaging probe is inserted within the localizable sheath when navigated within the luminal tree. Whenever an anatomical landmark (such as a bifurcation) is identified by the intra-operative imaging probe as it traverses the landmark, the operator observes whether the location of the tip of the localizable sheath is superimposed at the corresponding landmark on the pre-procedure images. Should there be a discrepancy, then the pre-procedure images are adjusted such that the tool is now superimposed at the landmark. In some embodiments, the adjustment is performed manually by the operator. In some embodiments, the adjustment is performed automatically by the navigation system. In some embodiments, the adjustment is performed in a semi-automatic manner—for example, the operator points at, or marks, on the pre-procedure images, the correct location (as indicated by the intra-operative imaging) of the distal tip, and the system then transforms the pre-procedure images so that the distal tip now appears superimposed upon them at the correct current location. As a result of the intra-procedural adjustment, the accuracy in navigating tools to desired locations is typically increased.

In some embodiments, once navigation upon the pre-procedure images indicates that the navigated tool has arrived at its target, the tool is retrieved from the main channel of the maneuverable and localizable sheath while the sheath remains in place. An intra-operative imaging probe is then inserted through the sheath to provide additional verification that its distal tip is indeed positioned at the desired location. The verification is typically desirable prior to performing a treatment. Verification by an intra-operative endoluminal imaging probe such as ultrasound, OCT or MRI is particularly useful because the probe is typically able to see through and beyond the walls of the lumen.

In the case of the lungs, many target locations (such as suspected lung masses and, separately, lymph nodes) are situated not within the airways but rather beyond their walls. Once the location of the distal tip of the sheath is verified by the imaging probe as pointing towards the target location, then the tools being applied at the target location may include ones that penetrate the bronchial wall. In the case of biopsying a suspected lung mass outside the bronchi, the tool may be (among others) a biopsy needle, or a "cork-screw" like "excavator" device that first penetrates the tissue and then extracts a sample of it. In the case of a lymph node, the tool being applied is typically a trans-bronchial aspiration needle.

In some embodiments, the aforementioned tool and imaging probe are employed simultaneously through a multi-channel sheath, should their outer diameters allow that.

F. Applying Aforementioned Embodiments to Treating Chronic Obstructive Pulmonary Disease (COPD)

Reference is now made to FIG. 7, which is a schematic illustration of a maneuverable sheath 76 being inserted through a plug 71 and toward a region 74 suffering from pulmonary disease, in accordance with an embodiment of the present invention.

In some embodiments, some of the aforementioned devices and methods are applied within the bronchial tree when treating COPD in general, and emphysema in particular.

In the artificially-induced suction of fluid trapped in an emphysematous lung region, it is typically preferable that the force of exhalation is applied within or close to the pocket(s) of trapped fluid. (Such pockets are also known as bulla in the singular and as bullae in the plural.) If exhalation is applied at a bronchial segment that is significantly proximal to the pocket(s), then it may in some cases cause the endobronchial walls in the airway leading to the pocket (i.e., bulla) to collapse, which will typically prevent the fluid already trapped in the pocket from being exhaled.

However, the pockets (i.e., bullae) are often large in their number and relatively small in their sizes (with the smaller ones that are still considered material typically being 1 cm in diameter). Therefore, arriving at each of them locally in order to exhale trapped fluid is typically difficult.

In some embodiments, the following steps are taken to effectively suction trapped fluid from one or more bullae situated in an emphysematous lung region 74 such as a lobe or a segment of a lobe:

1. An image of the patient's lungs in general, and of the emphysematous region(s) in particular, is produced by an imaging modality in which emphysematous regions 74 may be identified. Typically, the image is a CT image. In some embodiments, the image is produced via Vibration Response Imaging, for example using systems produced by DeepBreeze, Ltd. (Or Akiva, Israel). In some embodiments, the images are subsequently viewed on a computerized display. In some embodiments, the emphysematous region(s) is identified by a physician observing the images. Alternatively or additionally, specialized software (such as, for example, the Emphysema Profiler or the Pulmonary Workstation, both from Vida Diagnostics (Iowa City, Iowa, USA)) is used in identifying the emphysematous region(s). Subsequently, the emphysematous region(s) are marked or highlighted, manually by the physician or automatically by software, on the images. In some embodiments, an endobronchial path leading towards or to the emphysematous regions, and possibly to specific bullae within the region, is identified. In some embodiments, the path is marked or highlighted, manually by the physician or automatically by software, on the images.

2. The aforementioned images are registered to the lungs of the patient. In some embodiments, registration is performed using natural anatomical landmarks (also known as fiducials), for example as described by Solomon et al. in the article entitled "3D CT-Guided Bronchoscopy with Real-Time Electromagnetic Position Sensor," which is incorporated herein by reference. In some embodiments, registration is performed via the aforementioned tree-to-tree method. In some embodiments, images generated by an endobronchial imaging probe are co-registered with the CT images, with the co-registration performed in the manner described hereinabove.

3. An endobronchial plug 71 is placed via an endoscope 72 within an airway 73 leading to the emphysematous region. In some embodiments, the plug is placed under endoscopic vision. In some embodiments, the plug is placed at an airway leading to a lobe, a lobe segment, and/or a lobule. The plug is typically structured so that it attaches (e.g., via a stent or a spring-like mechanism, or via a balloon) to the inner walls of the airway in which it is placed, such that it prevents or hinders the flow of fluid between its distal and proximal sides. The plug typically has an opening 75 (e.g., a lid, a membrane, etc.), which is typically open when something is inserted therethrough, and which is typically closed (e.g., sealed) when nothing is inserted therethrough. Typically, the plug is penetrated and traversed by sheath 76, as described in step 4 below. In some embodiments, the plug is radiopaque in whole or in part so that it may be easily observed under fluoroscopy during the procedure.

4. Sheath 76 (which is typically maneuverable and localizable as described hereinabove) is inserted towards the emphysematous lung region 74. In some embodiments, an inner tube (not shown) is inserted through the main channel of the sheath to add to the sheath's pushability. In some embodiments, the sheath is inserted through an endoscope. Typically, the sheath is able to advance through the airway beyond a point beyond which the endoscope is unable to be inserted, either because of (a) the relative diameters of the endoscope and the opening in the plug, or (b) the relative diameters of the endoscope and the airway. The sheath traverses the plug, typically by protruding from a distal end of the endoscope, and further typically via opening 75 in the plug. The plug around the sheath typically remains sealed, such that it hinders or prevents the passage of fluid from its proximal side to its distal side and towards the emphysematous lung region. Once the sheath traverses the plug, its distal tip is typically no longer imaged by the bronchoscope. From that point and onwards, the sheath is typically maneuvered with the help of an image-guided navigation system so that it enters the targeted bullae one by one. Typically, the navigation of the sheath is facilitated by a location sensor 77 coupled to the distal end of the sheath. During the maneuvering, the distal tip of the sheath is presented overlaid on the aforementioned images generated by the CT. In some embodiments, images previously acquired by an endobronchial imaging probe are displayed at the current location of the sheath. In some embodiments, an endobronchial imaging probe is inserted through the sheath prior to activating suction, or in between activations of suction, or immediately after the activation of suction, or during the activation of suction, and the location of the distal portion of the sheath relative to a bulla is verified using images acquired by the imaging probe. In some embodiments, the sheath is observed during the procedure via fluoroscopy. In some embodiments, the sheath is also navigated under fluoroscopy, and not using an image-guided navigation system.

5. At its proximal side, the main channel of sheath 76 is connected to a fluid suction apparatus. In some embodiments, a second tool used for suction is inserted through the channel of the sheath. In some embodiments, the suction tool is of the type commonly used in diagnostic bronchoscopic procedures (i.e., not procedures for treating COPD). In some embodiments, the suction apparatus applies suction that is considerably weaker than suction typically applied in bronchoscopic procedures, in order to reduce the likelihood of undesirable clinical phenomena. Subsequent to the sheath being navigated to and then entering a targeted bulla in the emphysematous region, the suction apparatus is activated, typically momentarily, such that fluid is suctioned from the bulla. In some embodiments, the location of the distal tip of the sheath is verified to be within the bulla by co-utilization of an intra-operative imaging probe as disclosed hereinabove. In some embodiments, the suction process is repeated multiple times, one or more time per bulla. In some embodiments, the most distal bullae are suctioned first, followed by the more proximal bullae, so that the sequence may in some cases reduce the likelihood of the sheath causing pneumothorax by puncturing the pleura of the subjects lungs. In some embodiments, suction is also applied not within bullae. As a result of suction as in the aforementioned embodiments, typically fluid is gradually suctioned from the emphysematous lung region. Consequently, the emphysematous lung region may partially or fully collapse. That typically leads to a smaller residual volume to the lungs, which is a desirable effect as it leaves more room within the rib cage for the healthier section of the lungs to expand and contract during the respiratory cycle.

6. Sheath 76 is retrieved from emphysematous lung region 74. As the sheath crosses, from distal to proximal, the aforementioned endobronchial plug, the opening in the plug closes so that entrance of fluid into the emphysematous lung region is hindered or prevented.

7. Optionally, the above steps are repeated after a certain period (e.g., a few months) to allow for the exhalation of fluid that in the meanwhile may have accumulated in the emphysematous lung region. Such an accumulation may occur due to collateral ventilation from neighboring lung regions. In another embodiment, the above steps are repeated several times in the course of a single procedure, each time for a different emphysematous region within the lungs.

U.S. patent application Ser. No. 12/006,950, to Tolkowsky, filed Jan. 8, 2008 (published as US 20080167614), entitled "Endobronchial fluid exhaler devices and methods for use thereof," is incorporated herein by reference. In some embodiments, the apparatus and methods described therein are used in conjunction with the apparatus and methods described hereinabove.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. Apparatus for suctioning trapped fluid from one or more bullae situated in an emphysematous lung region of a subject, the apparatus comprising:
a plug configured to be placed in an airway of the subject, the airway leading to the emphysematous lung region, the plug defining an opening therethrough that is in an open state thereof when something is inserted through the opening and is in a closed state thereof when nothing is inserted through the opening;
a tool having a distal portion and a proximal portion that is proximal to the distal portion, the tool being configured to facilitate suctioning therethrough of the fluid trapped within the one or more bullae of the region, while the proximal portion of the tool is disposed within the opening through the plug; and
a navigation aid configured to facilitate suctioning through the tool of the fluid trapped within the one or more bullae of the emphysematous region, by, prior to suctioning through the tool being applied, facilitating navigation of the distal portion of the tool to respective individual bullae of the region,
the navigation aid comprising at least one navigation aid selected from the group consisting of:
an intra-operative, endoluminal imaging probe configured to be inserted by means of the tool and to verify the location of the tool with respect to the individual bullae by acquiring endoluminal images from within the emphysematous lung region, and
an image-guided navigation system that comprises a location sensor coupled to the distal portion of the tool, the navigation system being configured (a) using the location sensor, to sense a current location of the distal portion of the tool when the distal portion of the tool is within the emphysematous lung region, and (b) in response thereto, to generate an indication of the current location of the distal portion of the tool on a previously-acquired image of a portion of the subject's body that contains the emphysematous lung region.

2. The apparatus according to claim 1,
wherein the navigation aid comprises the endoluminal imaging probe, the endoluminal imaging probe being configured to verify the location of the tool with respect to the individual bullae.

3. The apparatus according to claim 2, wherein the tool comprises a sheath, the apparatus further comprising a second tool configured to be inserted through the sheath.

4. The apparatus according to claim 2, wherein the imaging probe is insertable through the tool.

5. The apparatus according to claim 1, wherein the navigation aid comprises the image-guided navigation system.

6. The apparatus according to claim 5, wherein the tool comprises a sheath and wherein the location sensor is attached to the sheath.

7. The apparatus according to claim 6, further comprising a tool configured to be inserted through the sheath.

8. The apparatus according to claim 5, further comprising a sheath, wherein the tool is configured to be inserted through the sheath.

9. The apparatus according to claim 8, wherein the location sensor is attached to the distal portion of the tool.

10. The apparatus according to claim 8, wherein the location sensor is coupled to the distal portion of the tool via the sheath.

11. The apparatus according to claim 10, wherein the location sensor is attached to the sheath.

12. The apparatus according to claim 5, wherein the image-guided navigation system comprises a control unit configured to generate the indication of the current location of the distal portion of the tool on the previously-acquired image of the portion of the subject's body by:
registering the previously-acquired image of the portion of the subject's body with a current position of the portion of the subject's body, and
generating the indication of the current location of the distal portion of the tool at a location within the registered image that corresponds to the sensed location of the distal portion of the tool.

13. The apparatus according to claim 5, further comprising an intra-operative, endoluminal imaging probe configured to verify the location of the tool with respect to the individual bullae by acquiring endoluminal images from within the emphysematous lung region.

14. The apparatus according to claim 1, further comprising an endoscope configured to be inserted into the airway, the endoscope being unable to be inserted through the opening, wherein the tool is configured to be inserted through the opening by protruding from a distal end of the endoscope.

15. The apparatus according to claim 1, wherein the tool is configured to suction fluid from within at least one of the individual bullae a plurality of times.

16. The apparatus according to claim 1, wherein the navigation aid is configured to successively facilitate navigation of the distal portion of the tool to a plurality of individual bullae within the emphysematous region, and the tool is configured to successively facilitate suctioning therethrough of fluid from within each of the plurality of individual bullae.

17. A method for suctioning trapped fluid from one or more bullae situated in an emphysematous lung region of a subject, the method comprising:
inserting a plug into an airway of the subject, the airway leading to the emphysematous lung region, the plug defining an opening therethrough that is in an open state thereof when something is inserted through the opening and is in a closed state thereof when nothing is inserted through the opening;
directing toward respective individual bullae of the region, a distal portion of a tool, the tool having a distal portion and a proximal portion that is proximal to the distal portion, the directing of the distal portion of the tool toward the bullae being performed by:
determining a location of the tool with respect to the respective individual bullae of the region; and
directing the distal portion of the tool to the respective individual bullae of the region, in response to the determined location of the tool; and
suctioning the fluid through the tool from within the respective individual bullae of the region, while the proximal portion of tool is disposed within the opening through the plug, and subsequent to the directing of the distal portion of the tool to the respective individual bullae of the region.

18. The method according to claim 17, wherein
determining the location of the tool with respect to respective individual bullae of the region comprises acquiring images from within the emphysematous lung region using an endoluminal imaging probe.

19. The method according to claim 17, wherein suctioning the fluid through the tool, subsequent to the directing of the distal portion of the tool to the respective individual bullae of the region, comprises using weaker suction to suction the fluid than would be used if the tool was not directed to the respective individual bullae of the region.

20. The method according to claim 17, wherein:
determining the location of the tool with respect to respective individual bullae of the region comprises:
providing a previously-acquired image of a portion of the subject's body that includes at least some of the region;
generating an indication of a location of the distal portion of the tool within the previously-acquired image, by sensing the location of the distal portion of the tool; and
directing the distal portion of the tool to the respective individual bullae of the region comprises directing the distal portion of the tool to the respective individual bullae of the region using the indication of the location of the distal portion within the previously-acquired image.

21. The method according to claim 20, wherein directing the distal portion of the tool toward respective individual bullae comprises inserting the tool through the airway via a sheath.

22. The method according to claim 20, wherein generating the indication of the location of the distal portion of the tool within the previously-acquired image comprises:
registering the previously-acquired image of the portion of the subject's body with a current position of the portion of the subject's body; and
generating an indication of the distal portion of the tool at a location within the registered image that corresponds to the sensed location of the distal portion of the tool.

23. The method according to claim 20, further comprising facilitating verification of the location of the tool with respect to the respective individual bullae by endoluminal imaging.

24. The method according to claim 17,
further comprising inserting an endoscope into the airway, wherein directing the distal portion of the tool toward respective individual bullae comprises advancing the tool via the endoscope, beyond a distal end of the endoscope, and
wherein the method does not comprise inserting the endoscope through the opening.

25. The method according to claim 17, wherein suctioning the fluid comprises suctioning fluid from within at least one of the respective individual bullae a plurality of times.

26. The method according to claim 25, wherein suctioning fluid from within at least one of the respective individual bullae the plurality of times comprises:
suctioning fluid from within the respective individual bullae a first time; and
suctioning fluid from within at least one of the respective individual bullae a second time, subsequent to further fluid having accumulated within the emphysematous lung region, after having suctioned fluid from within each of the respective individual bullae for the first time.

27. The method according to claim 17, wherein inserting the tool comprises inserting a sheath, the method further comprising inserting a second tool through the sheath.

28. The method according to claim 17, wherein directing the distal portion of the tool to the respective individual bullae of the region comprises successively directing the distal portion of the tool to a plurality of individual bullae of the region, and wherein suctioning the fluid through the tool from within the individual bullae of the region comprises successively suctioning fluid through the tool from within each of the plurality of individual bullae.

29. The method according to claim 17, wherein the tool includes an endoscopy tool, and wherein directing the tool toward the respective individual bullae comprises directing the endoscopy tool toward the respective individual bullae.

* * * * *